United States Patent [19]
Itoh et al.

[11] Patent Number: 5,270,463
[45] Date of Patent: Dec. 14, 1993

[54] HALOGENATED ALKOXYPHTHALOCYANINES

[75] Inventors: Hisato Itoh, Yokohama; Katashi Enomoto, Zushi; Takahisa Oguchi; Tutomu Nishizawa, both of Yokohama, all of Japan

[73] Assignees: Mitsui Toatsu Chemicals, Incorporated, Tokyo; Yamamoto Chemicals, Incorporated, Yao, both of Japan

[21] Appl. No.: 723,589

[22] Filed: Jul. 1, 1991

Related U.S. Application Data

[63] Continuation-in-part of Ser. No. 451,175, Dec. 15, 1989, Pat. No. 5,124,067.

[30] Foreign Application Priority Data

| Dec. 15, 1988 | [JP] | Japan | 63-314986 |
|---|---|---|---|
| Jan. 13, 1989 | [JP] | Japan | 1-4763 |
| Jan. 13, 1989 | [JP] | Japan | 1-4764 |
| Apr. 19, 1989 | [JP] | Japan | 1-97604 |

[51] Int. Cl.$^5$ .................. C09B 47/04; C09B 47/067; C09B 47/073
[52] U.S. Cl. ................... 540/136; 252/587; 359/358; 540/128; 540/142; 540/143
[58] Field of Search ............... 252/299.2, 299.61, 587, 252/600; 8/661; 106/410; 540/140, 142, 143, 136, 128

[56] References Cited
U.S. PATENT DOCUMENTS

| 2,739,151 | 3/1956 | Rösch et al. | 540/140 X |
|---|---|---|---|
| 3,291,746 | 12/1966 | Donoian et al. | 252/587 |
| 3,763,182 | 10/1973 | Horiguchi et al. | 8/661 X |
| 4,298,975 | 11/1981 | van der Veen et al. | 369/94 |
| 4,529,688 | 7/1985 | Law et al. | 540/140 X |
| 4,663,084 | 5/1987 | Shirai et al. | 252/600 |
| 4,769,307 | 9/1988 | Ozawa et al. | 430/270 |
| 4,960,538 | 10/1990 | Itoh et al. | 252/299.2 |
| 5,024,926 | 6/1991 | Itoh et al. | 540/140 X |
| 5,124,067 | 6/1992 | Itoh et al. | 252/299.2 |

FOREIGN PATENT DOCUMENTS

| 0353394 | 2/1990 | European Pat. Off. |
|---|---|---|
| 61-152769 | 7/1986 | Japan |
| 61-197280 | 9/1986 | Japan |
| 61-246091 | 11/1986 | Japan |
| 62-39286 | 2/1987 | Japan |

OTHER PUBLICATIONS

"Handbook of Chemical Synonyms and Tradenames", Edited by William Gardner, 8th Edition Rems & Enlarg. by E. T. Cooke et al., CRC Press, Inc., Boca Raton Fla., (1978) p. 161.

Primary Examiner—Richard D. Lovering
Attorney, Agent, or Firm—Oblon, Spivak, McClelland, Maier & Neustadt

[57] ABSTRACT

A method for preparing a halogenated alkoxyphthalocyanine represented by the formula (7)

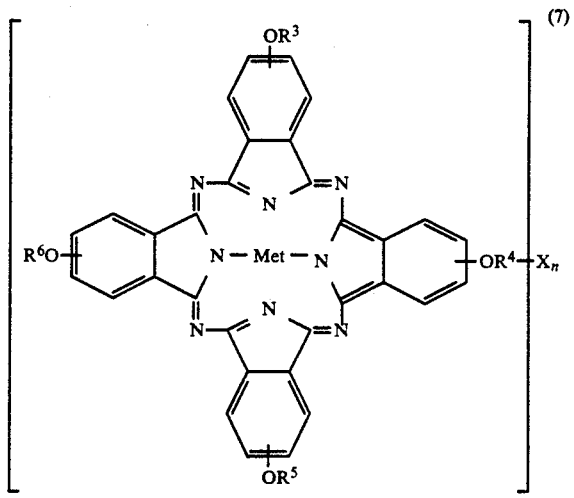

wherein $R^3$ to $R^6$ may be different and each of them is a secondary alkyl group, X is a halogen atom, n is the number of X and in the range of from 1 to 4, and Met is two hydrogen atoms, a divalent metal atom, or a triva- (Abstract continued on next page.)

lent or a tetravalent metallic derivative, which comprises the step of reacting a metal or a metallic compound with one to four kinds of raw materials selected from the group consisting of phthalonitriles represented by the following formula (1) and diiminoisoindolines represented by the following formula (2)

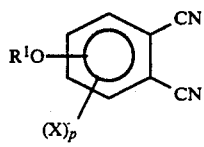 (1)

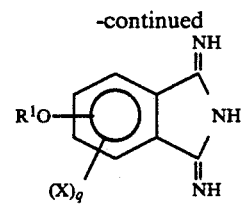 (2)

wherein $R^1$ is a secondary alkyl group, X is a halogen atom, and each of p and q is 0 or 1, but in at least one raw material, p or q is 1, and halogenated alkoxyphthalocyanine prepared by said method.

16 Claims, No Drawings

HALOGENATED ALKOXYPHTHALOCYANINES

This application is a continuation-in-part of application Ser. No. 07/451,175, filed Dec. 15, 1989 and now U.S. Pat. No. 5,124,067.

BACKGROUND OF THE INVENTION

1. Field of the Invention

The present invention relates to a method for preparing phthalocyanine analogous which are useful as a dye, a pigment, a photoelectric functional material and a recording/memory material, particularly a recording material for writable (recordable) compact discs, and it also relates to a phthalocyannne compound.

2. Description of the Related Art

Techniques by which a phthalocyanine is applied to an optical recording medium are described in U.S. Pat. No. 4,298,975, EP 353,394 and U.S. Pat. No. 4,769,307. However, the phthalocyanines disclosed in these patents are insufficient in points of sensitivity and refractive index as phthalocyanines for optical recording media.

Particularly, in the writable (recordable) compact discs (CD-WO), laser beams in the vicinity of 780 nm are utilized for writing and reading of records, and therefore it is important to control the absorptivity coefficient, the refractive index and the reflectance of a recording material at about 780 nm. Thus, it has been desired to develop phthalocyanines suitable for recording materials for CD-WO which have a good structure stability, a high refractive index for beams at about 780 nm, excellent resolution properties and a high sensitivity.

SUMMARY OF THE INVENTION

The present inventors have intensively researched to solve the above-mentioned problems, and as a result, they have found that a halogenated alkoxyphthalocyanine having a secondary alkoxy group and 1 to 4 halogen atoms is a compound suitable for the resolution of the above-mentioned problems. In consequence, the present invention has been achieved.

Accordingly, an object of the present invention is to provide a method for preparing the aforesaid halogenated alkoxyphthalocyanine.

Another object of the present invention is to provide a halogenated alkoxyphthalocyanine which is excellent as recording materials for CD-WO.

That is, the first aspect of the present invention is directed to a method for preparing a halogenated alkoxyphthalocyanine which comprises the step of reacting a metal or a metallic compound with 1 to 4 kinds of raw materials selected from the group consisting of phthalonitriles represented by the following formula (1)

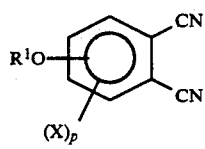

(1)

[wherein $R^1$ is a secondary alkyl group, X is a halogen atom, and p is 0 or 1, but in at least one raw material, p is 1] and diiminoisoindolines represented by the formula (2)

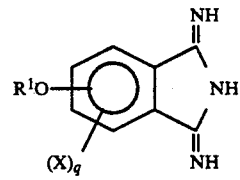

(2)

[wherein $R^1$ is a secondary alkyl group, X is a halogen atom, and q is 0 or 1, but in at least one raw material, q is 1].

The second aspect of the present invention is directed to a halogenated alkoxyphthalocyanine represented by the formula (7)

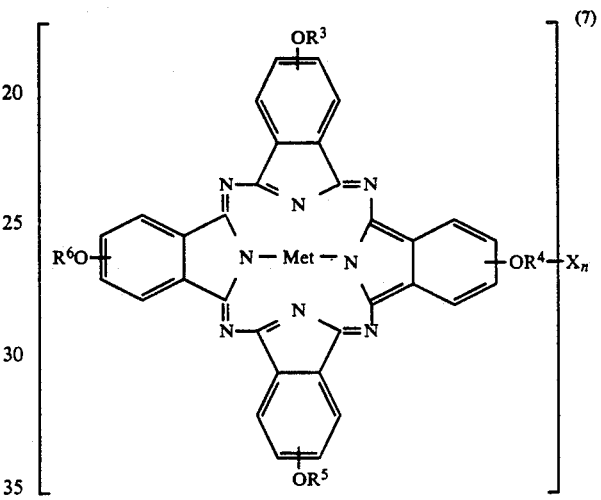

(7)

[wherein $R^3$–$R^6$ may be different and each of them is a secondary alkyl group, X is a halogen atom, n is the number of X and in the range of from 1 to 4, and Met is two hydrogen atoms, a divalent metal atom, or a trivalent or a tetravalent metallic derivative].

The particularly preferable halogenated alkoxyphthalocyanines are compounds in which the alkoxy group has 2 to 4 secondary, tertiary or quaternary carbon atoms in total and its preparation method have not been known.

DETAILED DESCRIPTION OF THE PREFERRED EMBODIMENTS

In the present invention, compounds which are preferable as raw materials include phthalonitriles represented by the formulae (3) and (4) as well as diiminoisoindolines represented by the formulae (5) and (6)

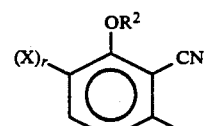

(3)

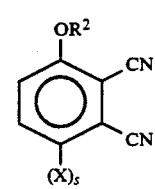

(4)

-continued

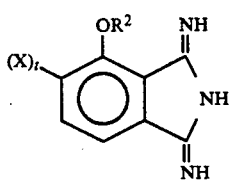
(5)

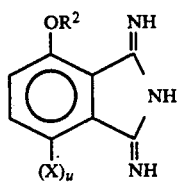
(6)

[wherein $R^2$ is a secondary alkyl group, X is a halogen atom, and each of r, s, t and u is 0 or 1, but in at least one raw material, r, s, t or u is 1].

The particularly preferable raw material is a compound represented by any of the formulae (3) to (6) in which $R^2$ is an alkyl group having 2 to 4 secondary, tertiary or quaternary carbon atoms in total, and X is bromine.

Examples of a metal or a metallic compound which is another raw material of the present invention include aluminum, silicon, titanium, vanadium, chromium, manganese, iron, cobalt, nickel, copper, zinc, gallium, germanium, ruthenium, rhodium, palladium, indium, tin and platinum, and chlorides, bromides, iodides, acetates and oxides of these metals. The particularly preferable examples include copper chloride, copper bromide, copper acetate, nickel chloride, nickel bromide, nickel acetate, palladium chloride, palladium bromide, palladium acetate, platinum chloride and platinum bromide.

A phthalocyanine ring can be synthesized by reacting 1-4 kinds of phthalonitriles and diiminoisoindolines which are the raw materials with the above-mentioned metal or metallic compound at a temperature of from 10° to 300° C. in a solvent, preferably an alcohol. When the raw materials are the phthalonitriles represented by the formulae (3) and/or (4), the reaction temperature is preferably in the range of from 80° to 160° C. Furthermore, when the raw materials are the diiminoisoindolines represented by the formulae (5) and/or (6), the reaction temperature is preferably in the range of from 140° to 200° C. Moreover, an auxiliary such as diazabicycloundecene (DBU) or diazabicyclononene (DBN) may be added as a catalyst for the ring formation.

Under the above-mentioned conditions, the halogenated alkoxyphthalocyanine of the above-mentioned formula (7) can be synthesized. The preferable halogenated alkoxyphthalocyanines are represented by the formulae (8) to (11)

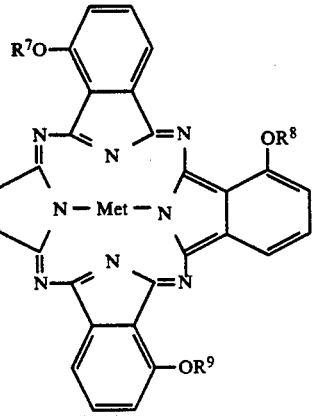
(8)

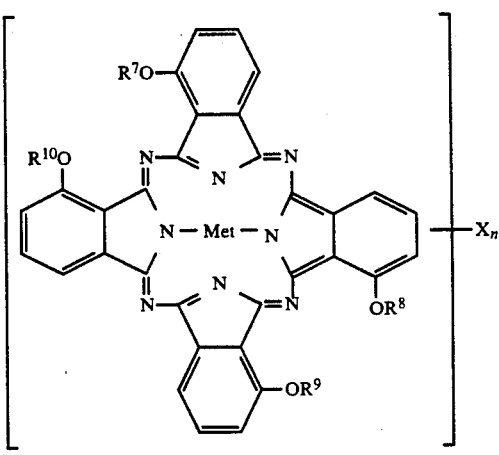
(9)

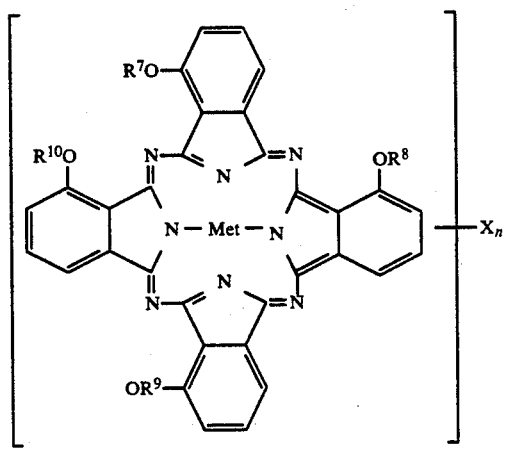
(10)

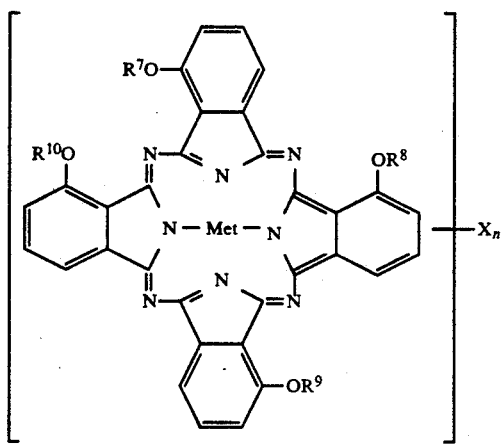

(11)

[wherein each of $R^7$ to $R^{10}$ is independently a secondary alkyl group, X is a halogen atom, n is the number of X and in the range of from 1 to 4, and Met is two hydrogen atoms, a divalent metal atom, or a trivalent or a tetravalent metallic derivative].

The particularly preferable halogenated alkoxyphthalocyanines are represented by the formulae (8) to (11) in which each of $R^7$ to $R^{10}$ is an alkyl group having 2 to 4 secondary, tertiary or quaternary carbon atoms in total, and X is a bromine atom.

In the present invention, the halogenated alkoxyphthalocyanine of each of the formulae (8) to (11) can be obtained in the form of one single compound or a mixture of two or more kinds of compounds.

Examples of the secondary alkyl group represented by $R^1$ to $R^{10}$ in the formulae (1) to (11) include hydrocarbon group such as an iso-propyl group, sec-butyl group, t-butyl group, neo-pentyl group, 1, 2-dimethylpropyl group, cyclo-hexyl group, 1, 3-dimethylbutyl group, 1-isopropylpropyl group, 1, 2-dimethylbutyl group, 1, 4-dimethylpentyl group, 2-methyl-1-isopropylpropyl group, 1-ethyl-3-methylbutyl group, 3-methyl-1-isopropylbutyl group, 2-methyl-1-iso-propylbutyl group and 1-t-butyl-2-methylpropyl group, and a halogenated alkyl group such as a 1, 1, 1, 3, 3, 3-hexafluoro-2-propyl group.

The phthalonitrile of the formula (1) or the diiminoisoindoline of the formula (2) which is used in the present invention can be synthesized by the procedure represented by the following reaction formula (12):

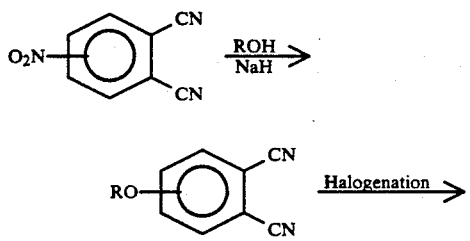

(12)

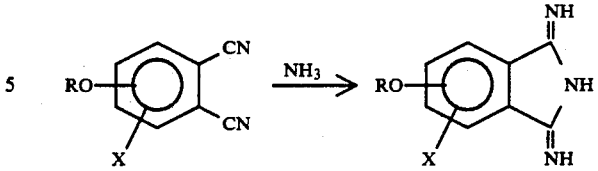

3-nitrophthalonitrile or 4-nitrophthalonitrile which was a starting material was a commercial product available from TOKYO KASEI KOGYO CO, LTD. The first reaction of from the nitrophthalonitrile to an alkoxyphthalo-nitrile was carried out referring to the process described in NOUVEAU JOUNAL DE CHIMIE, Vol. 6, No. 12, pp. 653-58, 1982. That is, sodium alkoxide which was obtained by reacting an alcohol with sodium hydride was reacted with the nitrophthalonitrile at 0°-100° C. to obtain the alkoxy-phthalonitrile.

The synthesis of a halogenated alkoxyphthalonitrile was effected by halogenating the alkoxyphthalonitrile in accordance with the method described in I. T. Harrison and S. Harrison, "COMPENDIUM OF ORGANIC SYNTHETIC METHOD", Vols. 1-6, Wiley-Interscience. Afterward, separation and purification were carried out through a column chromatoqraphy. Preferable examples of a halogenating agent which can be used in the above-mentioned halogenation include chlorine, bromine, iodine, sulfuryl chloride, thionyl chloride, antimony chloride, $ICl_3$, $FeCl_3$, phosphorus pentachloride, phosphorus oxychloride, t-butyl hypochlorite, N-chlorosuccinic imide, cupric bromide, quaternary ammonium bromide, N-bromosuccinic imide, iodine monochloride, quatornary ammonium iodide and potassium triiodide. The halogenating agent is suitably used in a molar ratio of from 1 to 2 per mole of the alkoxyphthalonitrile.

The halogenated alkoxyphthalocyanine of the present invention is suitable for the recording layer material of an optical recording medium.

An optical recording medium which comprises the halogenated alkoxyphthalocyanine described above, has good quality. The medium can be manufactured by the following process:

The medium is substantially composed of a transparent substrate and recording layer. If desired, the medium has also an optical reflective layer and a protective layer.

The substrate can be made from an optically transparent resin. Examples of such resin include acrylic resin, polyethylene resin and polycarbonate resin. Furthermore, the substrate may be surface-treated with a thermosetting resin or an ultraviolet-setting resin.

The recording layer can be prepared by coating the above compounds on the substrate. In the coating method, a binder resin and the above compounds are dissolved in a solvent so that concentration of the binder resin and the above compounds may be 20% by weight or less, preferably 0%, i.e., absent and 0.05 to 20% by weight, preferably 0.5 to 20% by weight, respectively, and then application is carried out by using a spin coater. The thickness of the recording layer is preferably from 50 to 300 nm.

Considering solvent resistance of the substrates, such a solvent as exemplified below is preferably used in the spin coating. Examples of such preferably usable solvents include halogenated hydrocarbons such as dichloromethane, chloroform, carbon tetrachloride, trichloroethane, dichloroethane, tetrachloroethylene and dichlorodifluoroethane; ethers such as diethyl ether, dipropyl ether, dibutyl ether and dioxane; alcohols such as methanol, ethanol, propanol and butanol; "CELLOSOLVES" brand name for ethanediol ethers and ether esters such as "METHYL CELLOSOLVE" a brand name for 2-methoxyethanol, "ETHYL CELLOSOLVE" a brand name for 2-ethoxyethanol "PROPYL CELLOSOLVE" a brand name for 2-butoxyethanol and "BUTYL CELLOSOLVE" a brand name for 2-butoxyethanol; ketones such as trifluoroacetone, hexafluoroacetone and hexafluoro-2-butanone; and hydrocarbons such as hexane, octane, cyclohexane and cyclooctane.

The reflective layer comprises aluminum or gold.

The reflective layer can be prepared by vapor depositing or sputtering. The thickness of the reflective layer is preferably 1 to 200 nm.

Preferred protective layer is transparency and can be prepared by applying an ultraviolet curing resin or thermosetting resin with a spin coater and then curing the resin. The thickness of the protective layer is preferably from 1 to 500 μm.

When the optical recording media are manufactured, it is preferred from the viewpoints of cost and users' handling that the polyacrylate or polycarbonate substrates are employed and that the application is made by the spin coating technique.

The present invention will hereinafter be illustrated in detail by way of examples. However, these examples are not construed to be limiting the scope of the invention. Part or parts used in the examples mean part or parts by weight.

EXAMPLE 1

A mixture of 10 parts of a phthalonitrile derivative represented by the following structural formula (1-1), 2 parts of PdCl$_2$, 4 parts of DBU and 200 parts of n-amyl alcohol was heated under reflux.

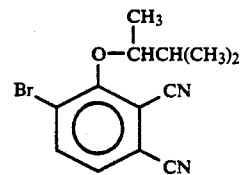
(1-1)

Afterward, the resulting reaction solution was poured into water, and the deposited tar was purified through column chromatography, so that 2.5 parts of a phthalocyanine compound represented by the following structural formula (3-1) was obtained (λmax=688 nm/hexane, εmax=2.4×10$^5$):

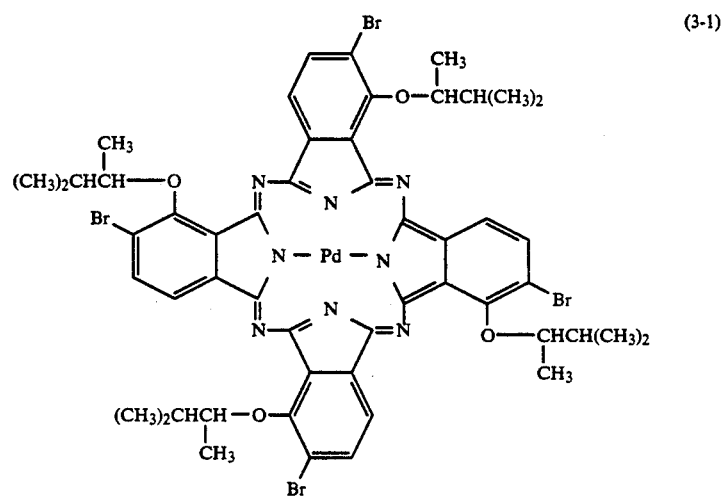

Results of element analysis (as Pd C$_{52}$H$_{52}$N$_8$O$_4$Br$_4$)

|  | C | H | N |
|---|---|---|---|
| Found (%) | 48.93 | 4.18 | 8.69 |
| Calcd. (%) | 48.82 | 4.07 | 8.76 |

One part of the obtained phthalocyanine compound (3-1) was dissolved in 100 parts of methylcyclohexane, and the resulting solution was then applied onto a polycarbonate substrate. Afterward, an acrylic UV setting resin was further applied and cured thereon, so that an optical card was prepared. This optical card had a reflectance of 32% and a sensitivity of 50 dB at 780 nm, 8 mW and a linear velocity of 1.8 m/sec.

EXAMPLE 2

A mixture of 10 parts of a phthalonitrile derivative represented by the following structural formula (1-2), 2 parts of PdCl$_2$, 4 parts of DBU and 200 parts of n-amyl alcohol was heated at 95° C.

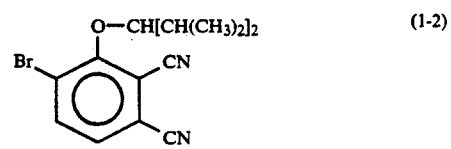
(1-2)

Afterward, the resulting reaction solution was poured into methanol, and the deposited tar was purified through column chromatography, so that 2.0 parts of a phthalocyanine compound represented by the following structural formula (3-2) (λmax=715 nm/toluene, εmax=2.2×10⁵) and 1.5 parts of a phthalocyanine compound represented by the following structural formula (3-3) (λmax=716 nm/toluene, εmax=2.2×10⁵) were obtained:

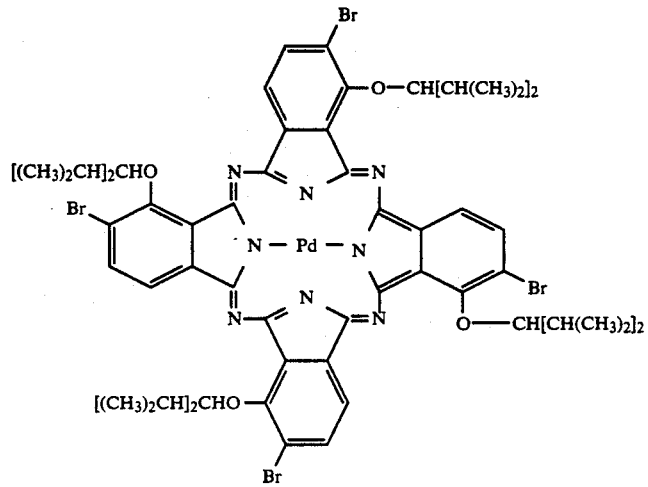

(3-2)

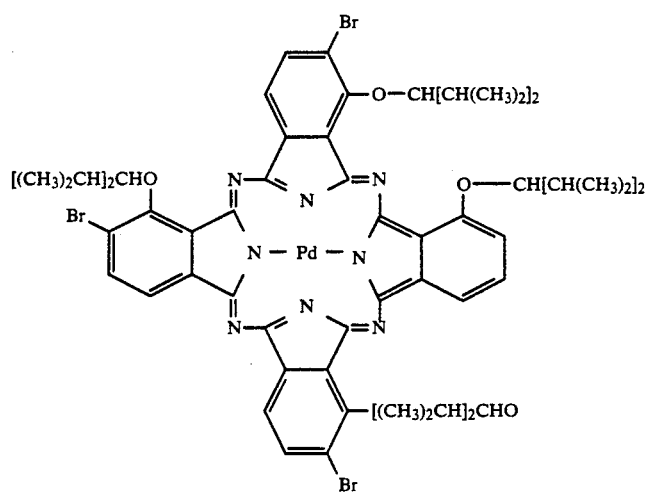

(3-3)

These phthalocyanines were identified by the element analysis and the mass spectrometry. The results are shown below.

Results of element analysis and mass spectrometry of the compound (3-2) (as Pd $C_{60}H_{68}N_8O_4Br_4$)
m/e=1391

|          | C     | H    | N    |
|----------|-------|------|------|
| Found (%) | 51.82 | 4.91 | 8.03 |
| Calcd. (%)| 51.80 | 4.93 | 8.05 |

Results of element analysis and mass spectrometry of the compound (3-3) (as Pd $C_{60}H_{68}N_8O_4Br_4$)
m/e=1391

|          | C     | H    | N    |
|----------|-------|------|------|
| Found (%) | 51.78 | 4.92 | 8.06 |
| Calcd. (%)| 51.80 | 4.93 | 8.05 |

The solution obtained by dissolving 3 parts of the phthalocyanine compound (3-2) in 100 parts of ethylcyclohexane was applied onto a polycarbonate substrate with a spin coater to obtain a film thickness of 120 nm. Afterward, gold was deposited on the coated layer by vapor deposition process and successively a protective layer was formed by using an ultraviolet curing resin, so that a optical recording medium was obtained.

This medium had a reflectance of 67% at 780 nm and a record having a C/N ratio of 58 dB could be written in the medium at a linear velocity of 1.8 m/sec with a laser beam of 7 mW in power and 785 nm in wavelength.

EXAMPLE 3

A mixture of 10 parts of a phthalonitrile derivative represented by the following structural formula (1-3), 2 parts of $PdCl_2$, 4 parts of DBU and 200 parts of n-amyl alcohol was heated at 110° C. for 8 hours.

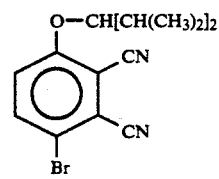

(1-3)

Afterward, the resulting reaction solution was poured into methanol, and the deposited tar was purified through column chromatography, so that 1 part of a phthalocyanine compound (3-4) (λmax=716 nm/toluene, εmax=2.2×10$^5$), 2.0 parts of a phthalocyanine compound (3-5) (λmax=716 nm/toluene, εmax=2.2×10$^5$) and 1 part of a phthalocyanine compound (3-6) (λmax=715 nm/toluene, εmax=2.2×10$^5$) were obtained. The structural formulae of these phthalocyanine compounds are shown below:

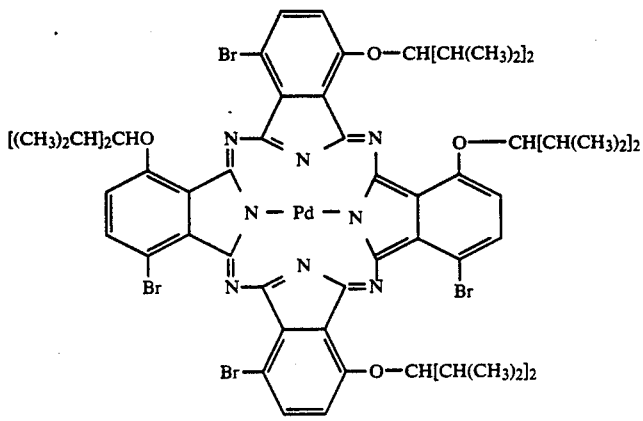

(3-4)

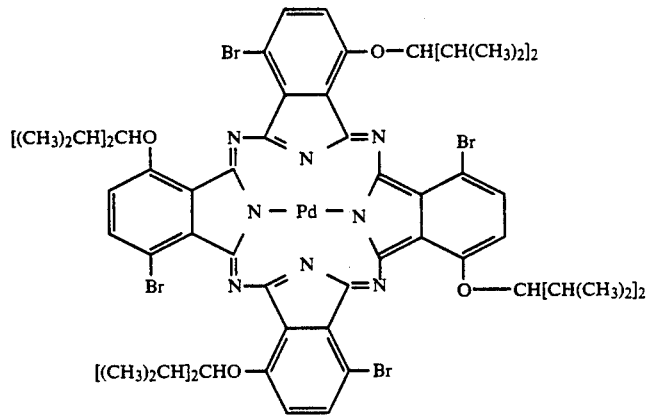

(3-5)

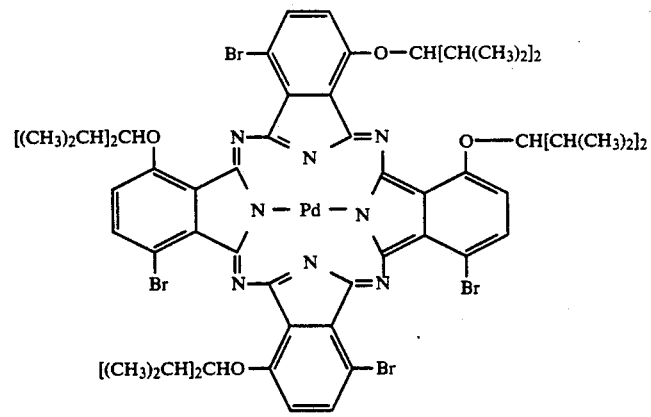

(3-6)

These phthalocyanine compounds were identified by the element analysis and the mass spectrometry. The results are shown below.

Results of lement analysis and mass spectrometry the element analysis and the mass spectrometry. The results are shown below.

Results of element analysis and mass spectrometry of the compound (3-4) (as Pd C$_{60}$H$_{68}$N$_8$O$_4$Br$_4$)
m/e=1391

|  | C | H | N |
|---|---|---|---|
| Found (%) | 51.83 | 4.90 | 8.03 |
| Calcd. (%) | 51.80 | 4.93 | 8.05 |

Results of element analysis and mass spectrometry of the compound (3-5) (as Pd C$_{60}$H$_{68}$N$_8$O$_4$Br$_4$)
m/e=1391

|  | C | H | N |
|---|---|---|---|
| Found (%) | 51.76 | 4.90 | 8.03 |

-continued

| | C | H | N |
|---|---|---|---|
| Calcd. (%) | 51.80 | 4.93 | 8.05 |

Results of element analysis and mass spectrometry of the compound (3-6) (as Pd $C_{60}H_{68}N_8O_4Br_4$)
m/e=1391

| | C | H | N |
|---|---|---|---|
| Found (%) | 51.81 | 4.94 | 8.03 |
| Calcd. (%) | 51.80 | 4.93 | 8.05 |

EXAMPLE 4

A mixture of 5 parts of the phthalonitrile derivative (1-2), 5 parts of the phthalonitrile derivative (1-3), 2 parts of $PdCl_2$, 4 parts of DBU and 300 parts of n-amyl alcohol was heated at 120° C. for 5 hours.

Afterward, the resulting reaction solution was poured into methanol, and the deposited tar was purified through column chromatography, so that 0.1 part of a phthalocyanine compound (3-7) ($\lambda max=716$ nm/toluene, $\epsilon max=2.2\times 10^5$), 0.1 part of a phthalocyanine compound (3-8) ($\lambda max=716$ nm/toluene, $\epsilon max=2.2\times 10^5$), 0.5 part of a phthalocyanine compound (3-9) ($\lambda max=716$ nm/toluene, $\epsilon max=2.2\times 10^5$), 0.3 part of a phthalocyanine compound (3-10) ($\lambda max=715$ nm/toluene, $\epsilon max=2.2\times 10^5$), 0.2 part of the phthalocyanine compound (3-2) and 0.2 part of the phthalocyanine compound (3-4) were obtained. The structural formulae of these phthalocyanine compounds, i.e., (3-7), (3-8), (3-9) and (3-10), are shown below:

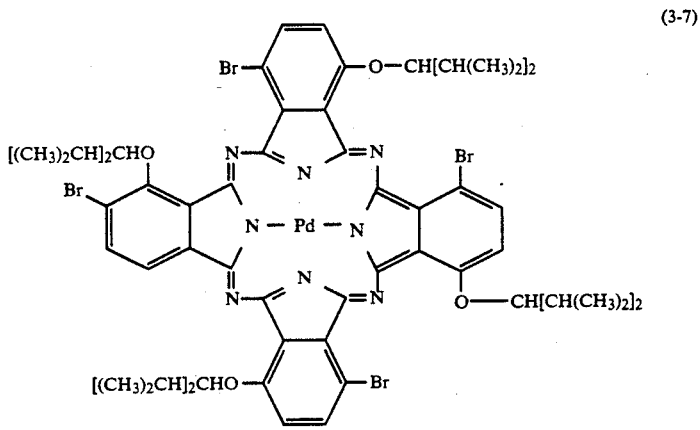

(3-7)

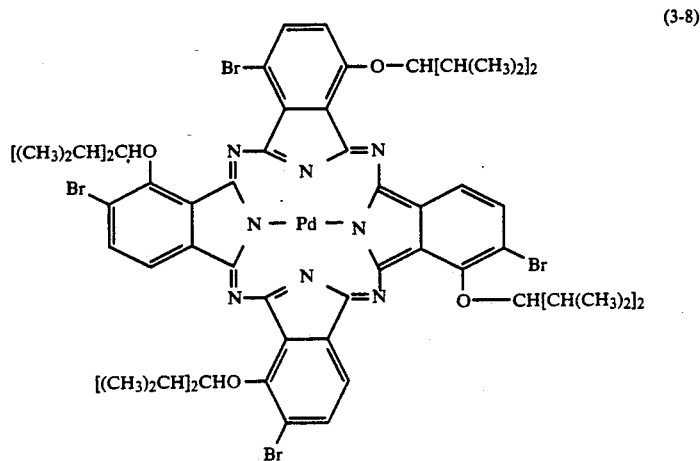

(3-8)

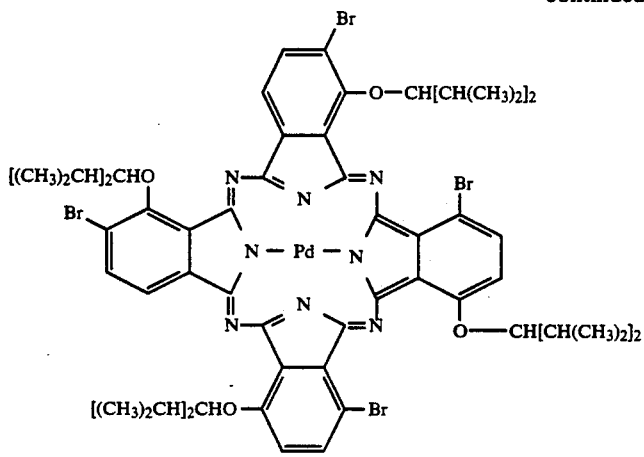

(3-9)

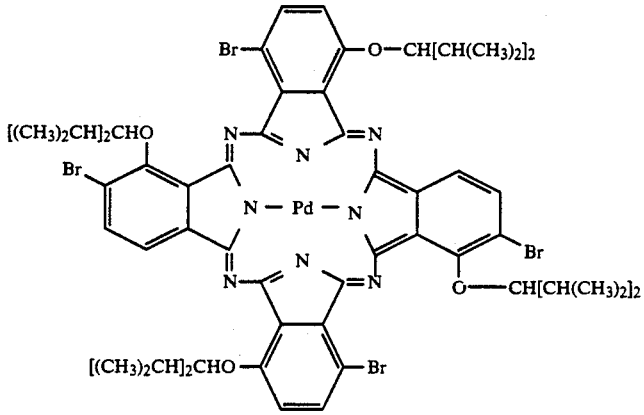

(3-10)

These phthalocyanine compounds were identified by the element analysis and the mass spectrometry. The results are shown below.

Results of element analysis and mass spectrometry of the compound (3-7) (as Pd $C_{60}H_{68}N_8O_4Br_4$)
m/e = 1391

|  | C | H | N |
|---|---|---|---|
| Found (%) | 51.67 | 4.95 | 8.10 |
| Calcd. (%) | 51.80 | 4.93 | 8.05 |

Results of element analysis and mass spectrometry of the compound (3-8) (as Pd $C_{60}H_{68}N_8O_4Br_4$)
m/e = 1391

|  | C | H | N |
|---|---|---|---|
| Found (%) | 51.90 | 4.88 | 7.99 |
| Calcd. (%) | 51.80 | 4.93 | 8.05 |

Results of element analysis and mass spectrometry of the compound (3-9) (as Pd $C_{60}H_{68}N_8O_4Br_4$)
m/e = 1391

|  | C | H | N |
|---|---|---|---|
| Found (%) | 51.85 | 4.87 | 8.11 |
| Calcd. (%) | 51.80 | 4.93 | 8.05 |

Results of element analysis and mass spectrometry of the compound (3-10) (as Pd $C_{60}H_{68}N_8O_4Br_4$)
m/e = 1391

|  | C | H | N |
|---|---|---|---|
| Found (%) | 51.78 | 4.87 | 7.99 |
| Calcd. (%) | 51.80 | 4.93 | 8.05 |

EXAMPLE 5

A mixture of 8 parts of the phthalonitrile derivative (1-2), 2 parts of a phthalonitrile derivative represented by the following structural formula (1-4), 2 parts of $PdCl_2$, 4 parts of DBU and 300 parts of n-amyl alcohol was heated at 100° C. for 10 hours.

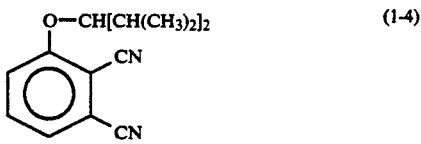

(1-4)

Afterward, the resulting reaction solution was poured into methanol, and the deposited tar was purified through column chromatography, so that 0.2 part of a phthalocyanine compound (3-11) (λmax = 700 nm/toluene, εmax = 2.3 × 10$^5$), 0.3 part of a phthalocyanine compound (3-12) (λmax = 705 nm/toluene, εmax = 2.2 × 10$^5$), 0.5 part of a phthalocyanine compound (3-13) (λmax = 700 nm/toluene, $\epsilon$max=2.3×10$^5$), 0.3 part of a phthalocyanine compound (3-14) ($\lambda$max=706 nm/toluene, $\epsilon$max=2.2×10$^5$), 0.2 part of a phthalocyanine compound (3-15) ($\lambda$max=699 nm/toluene, $\epsilon$max=2.2×10$^5$), 0.2 part of the phthalocyanine compound (3-2) and 0.2 part of the phthalocyanine compound (3-3) were obtained. The structural formulae of these phthalocyanine compounds, i.e., (3-11), (3-12), (3-13), (3-14) and (3-15), are shown below:

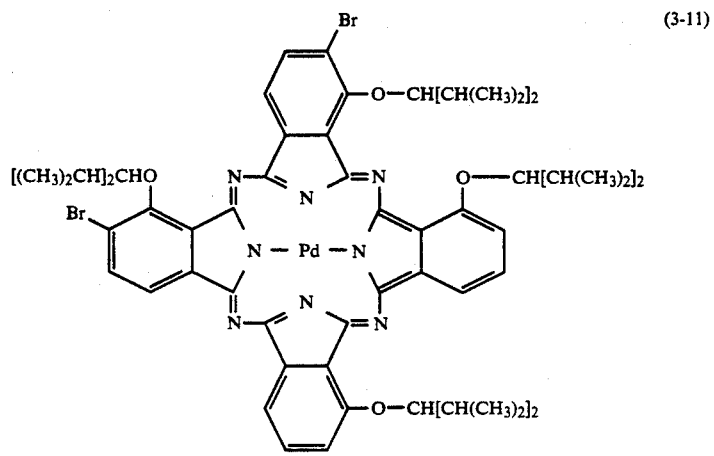

(3-11)

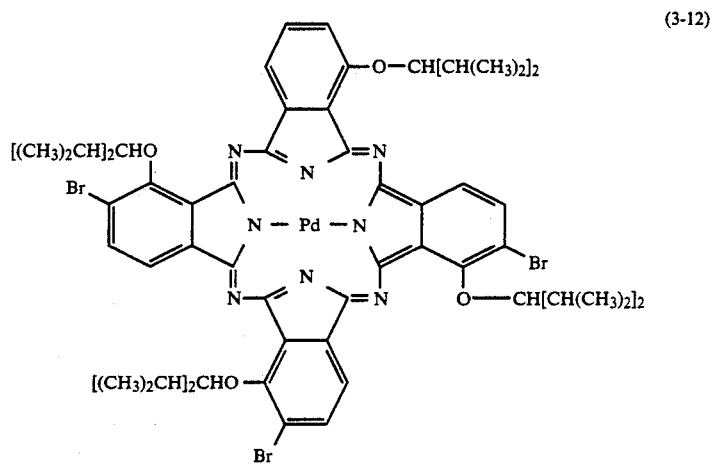

(3-12)

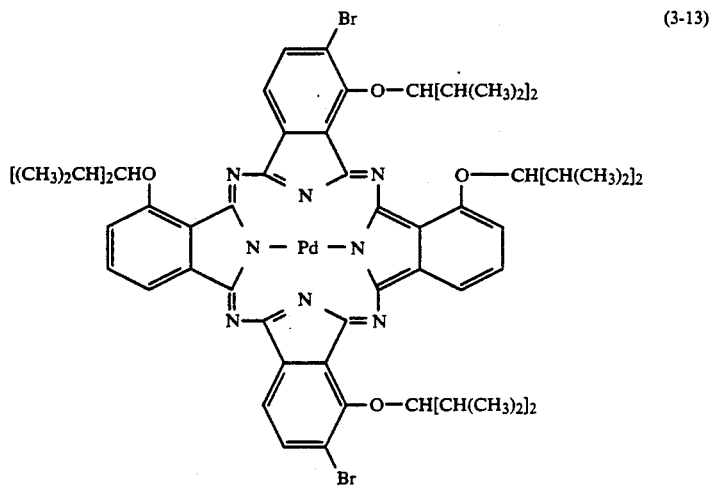

(3-13)

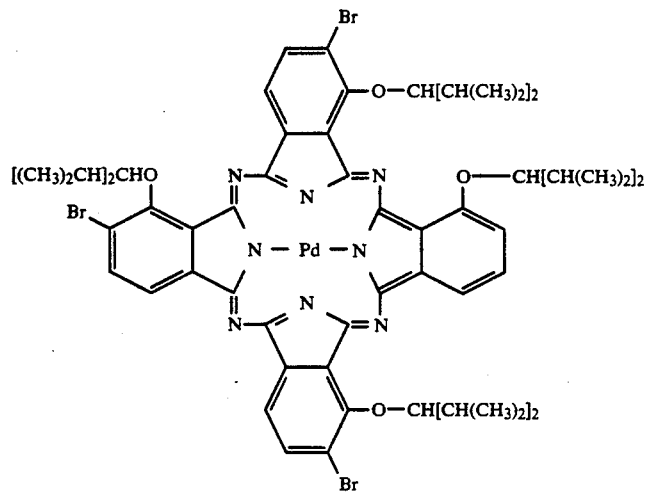

(3-14)

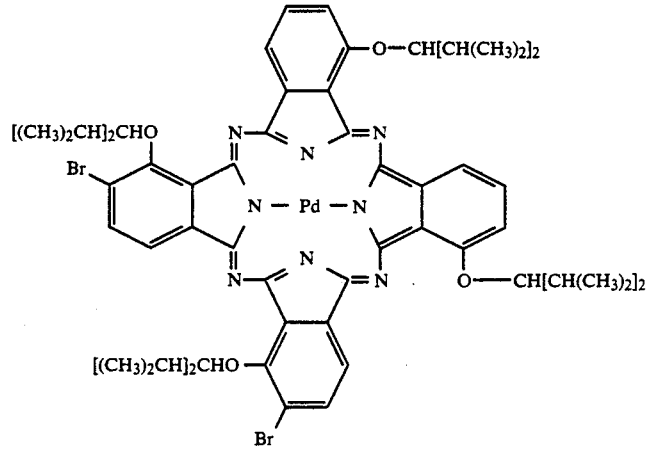

(3-15)

These phthalocyanine compounds were identified by the element analysis and the mass spectrometry. The results are shown below.

Results of element analysis and mass spectrometry of the compound (3-11) (as Pd $C_{60}H_{70}N_8O_4Br_2$)
m/e = 1233

|  | C | H | N |
|---|---|---|---|
| Found (%) | 58.22 | 5.90 | 9.10 |
| Calcd. (%) | 58.42 | 5.72 | 9.08 |

Results of element analysis and mass spectrometry of the compound (3-12) (as Pd $C_{60}H_{69}N_8O_4Br_3$)
m/e = 1312

|  | C | H | N |
|---|---|---|---|
| Found (%) | 54.90 | 5.41 | 8.12 |
| Calcd. (%) | 54.91 | 5.30 | 8.54 |

Results of element analysis and mass spectrometry of the compound (3-13) (as Pd $C_{60}H_{70}N_8O_4Br_2$)
m/e = 1233

|  | C | H | N |
|---|---|---|---|
| Found (%) | 58.01 | 5.87 | 9.11 |
| Calcd. (%) | 58.42 | 5.72 | 9.08 |

Results of element analysis and mass spectrometry of the compound (3-14) (as Pd $C_{60}H_{69}N_8O_4Br_3$)
m/e = 1312

|  | C | H | N |
|---|---|---|---|
| Found (%) | 54.78 | 5.57 | 8.38 |
| Calcd. (%) | 54.91 | 5.30 | 8.54 |

Results of element analysis and mass spectrometry of the compound (3-15) (as Pd $C_{60}H_{70}N_8O_4Br_2$)
m/e = 1233

|  | C | H | N |
|---|---|---|---|
| Found (%) | 58.23 | 5.59 | 8.98 |
| Calcd. (%) | 58.42 | 5.72 | 9.08 |

EXAMPLE 6

A mixture of 7 parts of a diimino-iso-indoline derivative (2-1), 3 parts of the phthalonitrile derivative (1-4), 2 parts of PdCl$_2$, 4 parts of DBU and 300 parts of n-octyl alcohol was heated at 180° C. for 10 hours.

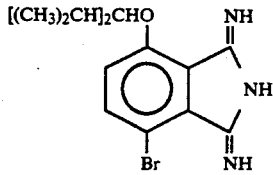
(2-1)

Afterward, the resulting reaction solution was poured into methanol, and the deposited tar was purified through column chromatography, so that 0.4 part of a phthalocyanine compound (3-16) (λmax=698 nm/toluene, εmax=2.3×10$^5$), 0.3 part Of a phthalocyanine compound (3-17) (λmax=705 nm/toluene, εmax=2.2×10$^5$), 0.2 part of a phthalocyanine compound (3-18) (λmax= 699 nm/toluene, εmax=2.3×10$^5$), 0.2 part of a phthalocyanine compound (3-19) (λmax=707 nm/toluene, εmax=2.2×10$^5$), 0.2 part of a phthalocyanine compound (3-20) (λmax=698 nm/toluene, εmax=2.2×10$^5$), 0.1 part of a phthalocyanine compound (3-21) (λmax=694 nm/toluene, εmax=2.3×10$^5$), 0.2 part of a phthalocyanine compound (3-22) (λmax=695 nm/toluene, εmax=2.2×10$^5$), 0.2 part of the phthalocyanine compound (3-4) and 0.2 part of the phthalocyanine compound (3-5) were obtained. The structural formulae of these phthalocyanine compounds, i.e., (3-16), (3-17), (3-18), (3-19), (3-20), (3-21) and (3-22), are shown below:

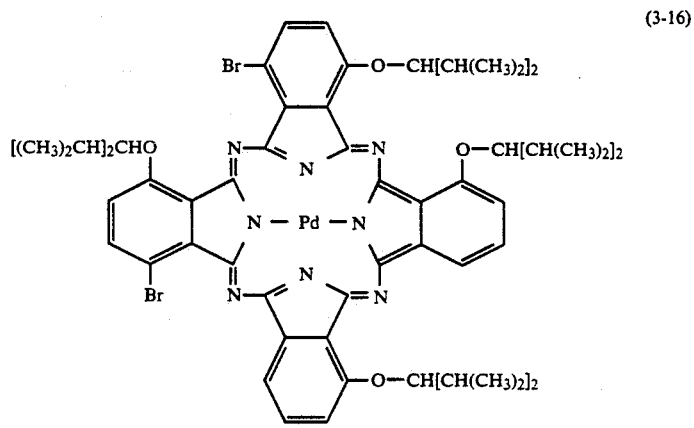
(3-16)

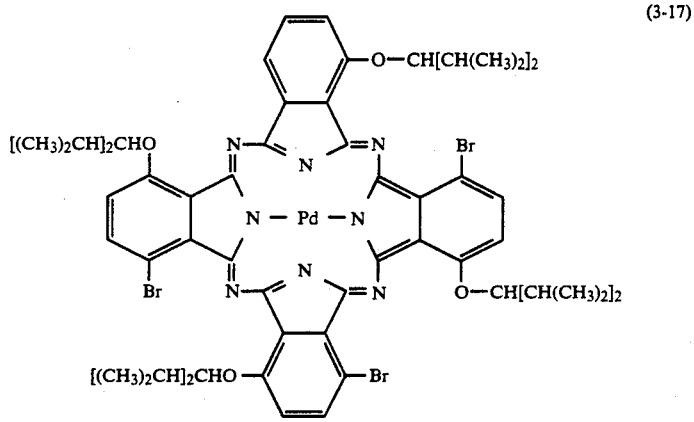
(3-17)

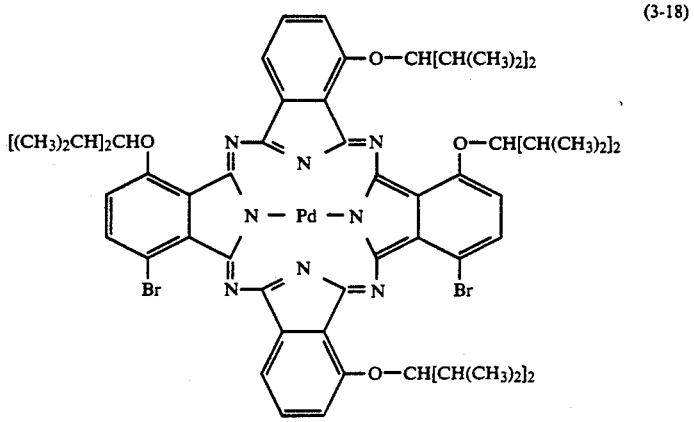
(3-18)

-continued
(3-19)
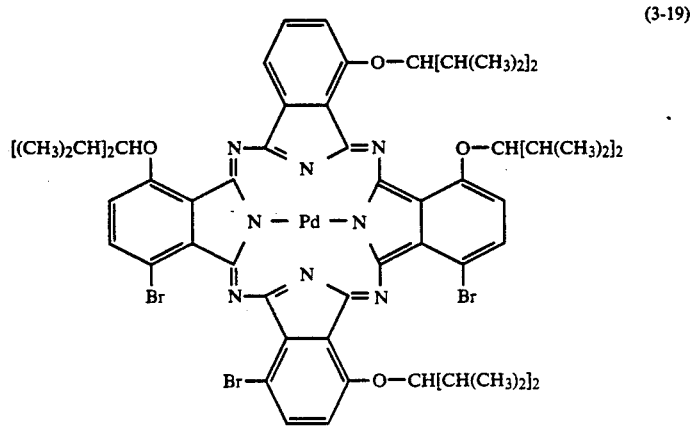
(3-20)
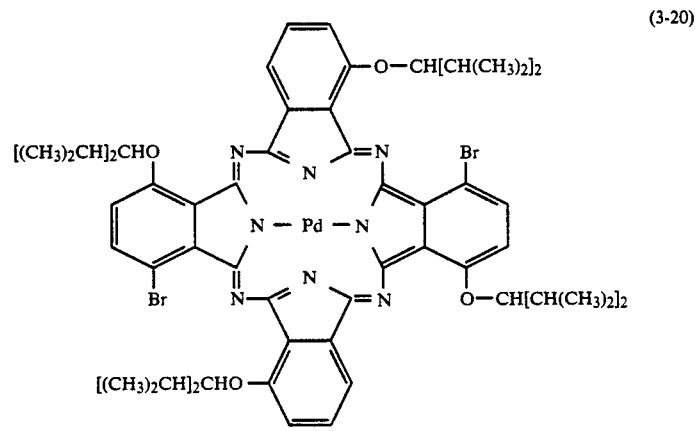
(3-21)
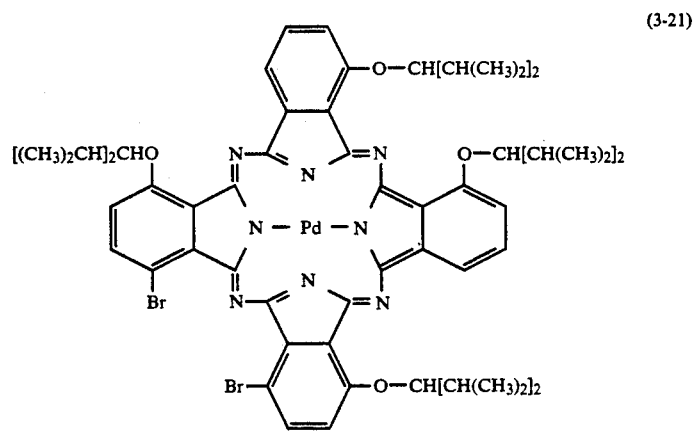

-continued

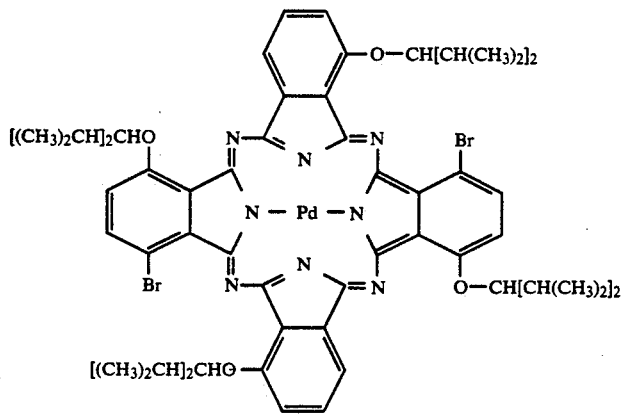
(3-22)

These phthalocyanine compounds were identified by the element analysis and the mass spectrometry. The results are shown below.

Results of element analysis and mass spectrometry of the compound (3-16) (as Pd $C_{60}H_{70}N_8O_4Br_2$) m/e=1233

|  | C | H | N |
|---|---|---|---|
| Found (%) | 58.31 | 5.87 | 9.01 |
| Calcd. (%) | 58.42 | 5.72 | 9.08 |

Results of element analysis and mass spectrometry of the compound (3-17) (as Pd $C_{60}H_{69}N_8O_4Br_3$) m/e = 1312

|  | C | H | N |
|---|---|---|---|
| Found (%) | 54.98 | 5.28 | 8.61 |
| Calcd. (%) | 54.91 | 5.30 | 8.54 |

Results of element analysis and mass spectrometry of the compound (3-18) (as Pd $C_{60}H_{70}N_8O_4Br_2$) m/e=1233

|  | C | H | N |
|---|---|---|---|
| Found (%) | 58.52 | 5.66 | 9.03 |
| Calcd. (%) | 58.42 | 5.72 | 9.08 |

Results of element analysis and mass spectrometry of the compound (3-19) (as Pd $C_{60}H_{69}N_8O_4Br_3$) m/e=1312

|  | C | H | N |
|---|---|---|---|
| Found (%) | 55.01 | 5.27 | 8.48 |
| Calcd. (%) | 54.91 | 5.30 | 8.54 |

Results of element analysis and mass spectrometry of the compound (3-20) (as Pd $C_{60}H_{70}N_8O_4Br_2$) m/e=1233

|  | C | H | N |
|---|---|---|---|
| Found (%) | 58.33 | 5.79 | 9.15 |
| Calcd. (%) | 58.42 | 5.72 | 9.08 |

Results of element analysis and mass spectrometry of the compound (3-21) (as Pd $C_{60}H_{71}N_8O_4Br_1$) m/e=1154

|  | C | H | N |
|---|---|---|---|
| Found (%) | 62.21 | 6.27 | 9.48 |
| Calcd. (%) | 62.41 | 6.20 | 9.70 |

Results of element analysis and mass spectrometry of the compound (3-22) (as Pd $C_{60}H_{71}N_8O_4Br_1$) m/e=1154

|  | C | H | N |
|---|---|---|---|
| Found (%) | 62.63 | 6.79 | 9.15 |
| Calcd. (%) | 62.41 | 6.20 | 9.70 |

EXAMPLE 7

A mixture of 7 parts of a diimino-iso-indoline derivative (2-2), 3 parts of a diimino-iso-indoline derivative (2-3), 2 parts of PdCl₂, 4 parts of DBU and 300 parts of n-octyl alcohol was heated at 175° C. for 12 hours.

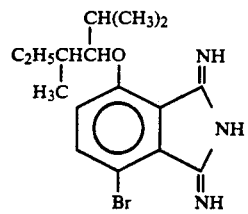
(2-2)

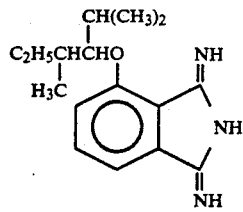
(2-3)

Afterward, the resulting reaction solution was poured into methanol, and the deposited tar was purified through column chromatography, so that 0.3 part of a phthalocyanine compound (3-23) ($\lambda$max=698 nm/toluene, $\epsilon$max=2.3×10⁵), 0.4 part of a phthalocyanine compound (3-24) ($\epsilon$max=704 nm/toluene, $\epsilon max = 2.2 \times 10^5$), 0.2 part of a phthalocyanine compound (3-25) ($\lambda max = 700$ nm/toluene, $\epsilon max = 2.3 \times 10^5$), 0.2 part of a phthalocyanine compound (3-26) ($\lambda max = 707$ nm/toluene, $\epsilon max = 2.2 \times 10^5$), 0.2 part of a phthalocyanine compound (3-27) ($\lambda max = 699$ nm/toluene, $\epsilon max = 2.2 \times 10^5$), 0.1 part of a phthalocyanine compound (3-28) ($\lambda max = 694$ nm/toluene, $\epsilon max = 2.3 \times 10^5$), 0.2 part of a phthalocyanine compound (3-29) ($\lambda max = 694$ nm/toluene, $\epsilon max = 2.2 \times 10^5$), 0.2 part of a phthalocyanine compound (3-30) ($\lambda max = 715$ nm/toluene, $\epsilon max = 2.1 \times 10^5$) and 0.2 part of a phthalocyanine compound (3-31) ($\lambda max = 714$ nm/toluene, $\epsilon max = 2.1 \times 10^5$) were obtained. The structural formulae of these phthalocyanine compounds, i.e., (3-23), (3-24), (3-25), (3-26), (3-27), (3-28), (3-29), (3-30) and (3-31), are shown below:

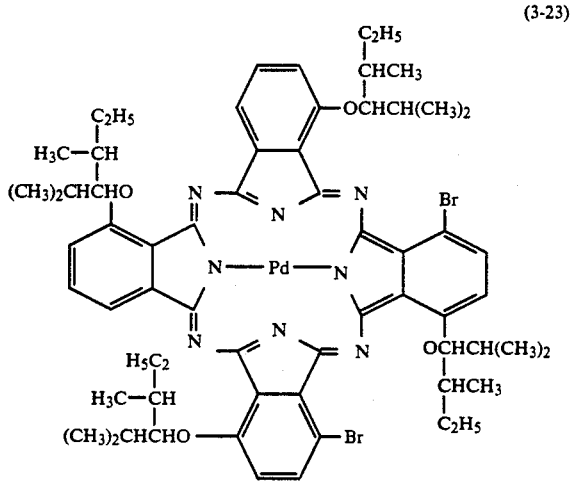

(3-23)

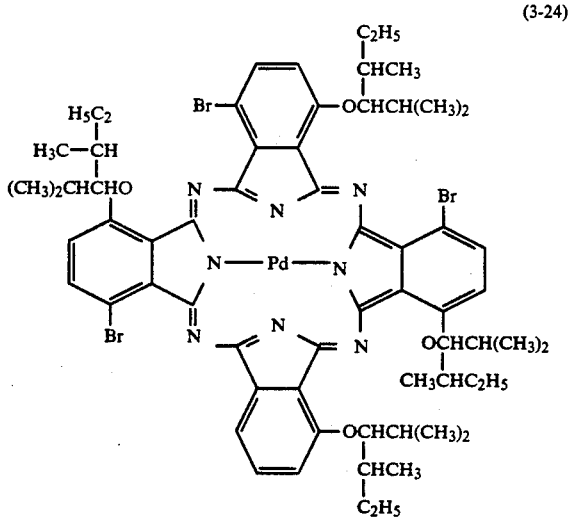

(3-24)

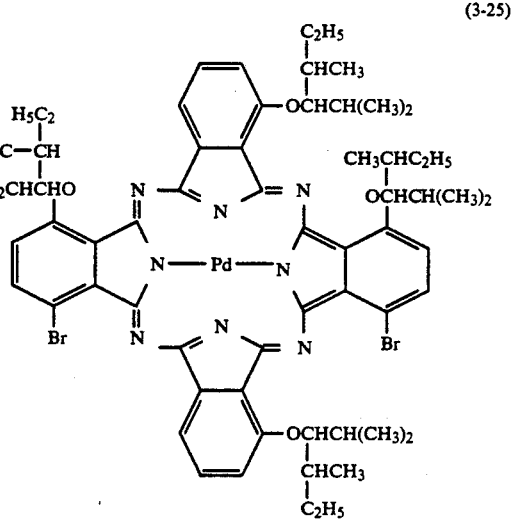

(3-25)

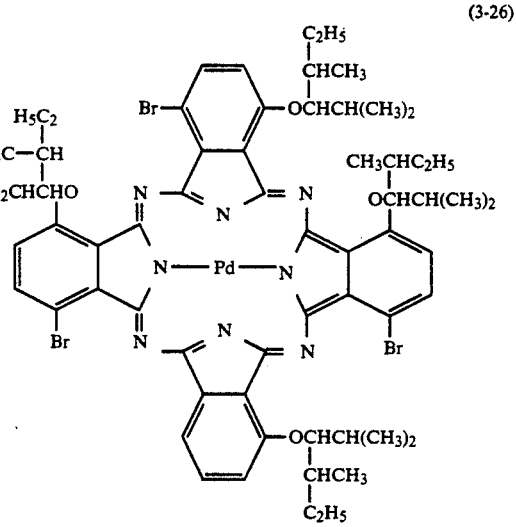

(3-26)

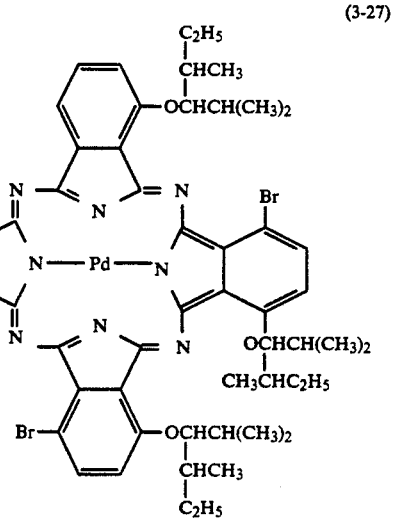

(3-27)

-continued (3-28)

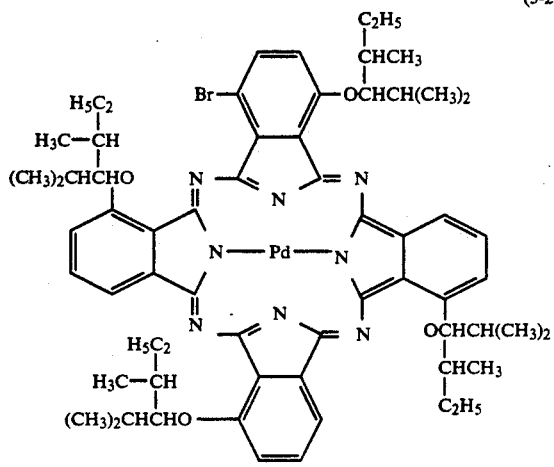

(3-29)

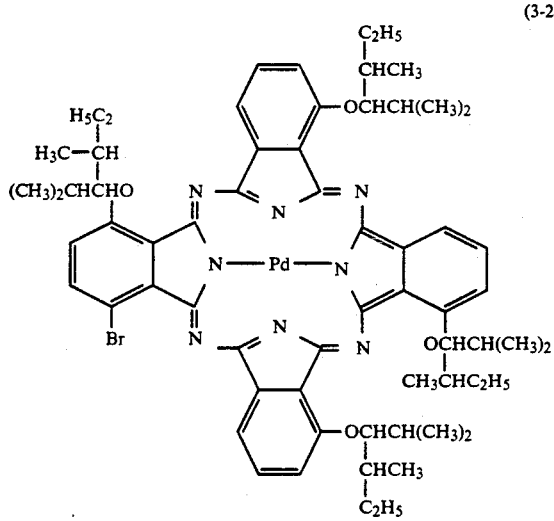

(3-30)

-continued (3-31)

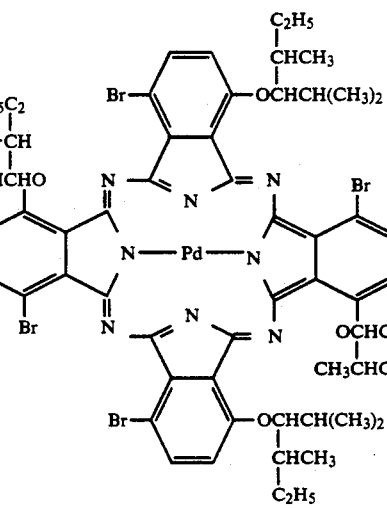

These phthalocyanine compopunds were identified by the element analysis and the mass spectrometry. The results are shown below.

Results of element analysis and mass spectrometry of the compound (3-23) (as Pd $C_{64}H_{78}N_8O_4Br_2$)
m/e=1289

|           | C     | H    | N    |
|-----------|-------|------|------|
| Found (%) | 59.11 | 5.97 | 8.51 |
| Calcd. (%)| 59.61 | 6.10 | 8.69 |

Results of element analysis and mass spectrometry of the compound (3-24) (as Pd $C_{64}H_{77}N_8O_4Br_3$)
m/e=1364

|           | C     | H    | N    |
|-----------|-------|------|------|
| Found (%) | 55.98 | 5.28 | 8.32 |
| Calcd. (%)| 56.16 | 5.67 | 8.19 |

Results of element analysis and mass spectrometry of the compound (3-25) (as Pd $C_{64}H_{78}N_8O_4Br_2$)
m/e=1289

|           | C     | H    | N    |
|-----------|-------|------|------|
| Found (%) | 59.52 | 5.96 | 8.73 |
| Calcd. (%)| 59.61 | 6.10 | 8.69 |

Results of element analysis and mass spectrometry of the compound (3-26) (as Pd $C_{64}H_{77}N_8O_4Br_3$)
m/e=1368

|           | C     | H    | N    |
|-----------|-------|------|------|
| Found (%) | 56.01 | 5.27 | 8.48 |
| Calcd. (%)| 56.16 | 5.67 | 8.19 |

Results of element analysis and mass spectrometry of the compound (3-27) (as Pd $C_{64}H_{78}N_8O_4Br_2$)
m/e=1289

|           | C     | H    | N    |
|-----------|-------|------|------|
| Found (%) | 59.33 | 5.99 | 8.45 |

-continued

|  | C | H | N |
|---|---|---|---|
| Calcd. (%) | 59.61 | 6.10 | 8.69 |

Results of element analysis and mass spectrometry of the compound (3-28) (as Pd $C_{64}H_{79}N_8O_4Br_1$)
m/e = 1210

|  | C | H | N |
|---|---|---|---|
| Found (%) | 63.21 | 6.47 | 9.38 |
| Calcd. (%) | 63.49 | 6.58 | 9.26 |

Results of element analysis and mass spectrometry of the compound (3-29) (as Pd $C_{64}H_{79}N_8O_4Br_1$)
m/e = 1210

|  | C | H | N |
|---|---|---|---|
| Found (%) | 63.63 | 6.79 | 9.15 |
| Calcd. (%) | 63.49 | 6.58 | 9.26 |

Results of element analysis and mass spectrometry of the compound (3-30) (as Pd $C_{64}H_{76}N_8O_4Br_4$)
m/e = 1447

|  | C | H | N |
|---|---|---|---|
| Found (%) | 53.21 | 5.47 | 7.38 |
| Calcd. (%) | 53.11 | 5 29 | 7.74 |

Results of element analysis and mass spectrometry of the compound (3-31) (as Pd $C_{64}H_{76}N_8O_4Br_4$)
m/e = 1447

|  | C | H | N |
|---|---|---|---|
| Found (%) | 53.02 | 5.18 | 7.81 |
| Calcd. (%) | 53.11 | 5.29 | 7.74 |

EXAMPLE 8

A mixture of 7 parts of a diimino-iso-indoline derivative (2-4), 3 parts of a diimino-iso-indoline derivative (2-5), 2 parts of $PdCl_2$, 12, 4 parts of DBU and 300 parts of n-octyl alcohol was heated at 175° C. for 12 hours.

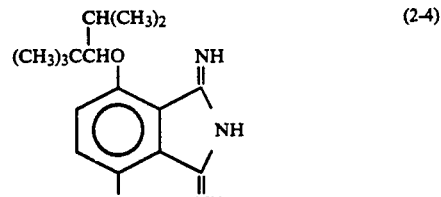
(2-4)

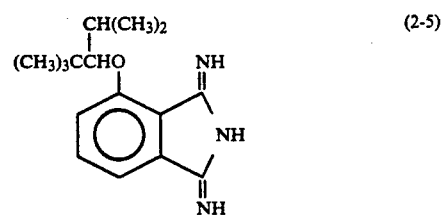
(2-5)

Afterward, the resulting reaction solution was poured into methanol, and the deposited tar was purified through column chromatography, so that 0.2 part of a phthalocyanine compound (3-32) ($\lambda$max = 702 nm/toluene, $\epsilon$max = 2.3 × 10$^5$), 0.4 part of a phthalocyanine compound (3-33) ($\lambda$max = 709 nm/toluene, $\epsilon$max = 2.2 × 10$^5$), 0.1 part of a phthalocyanine compound (3-34) ($\lambda$max = 705 nm/toluene, $\epsilon$max = 2.3 × 10$^5$), 0.1 part of a phthalocyanine compound (3-35) ($\lambda$max = 709 nm/toluene, $\epsilon$max = 2.2 × 10$^5$), 0.2 part of a phthalocyanine compound (3-36) ($\lambda$max = 703 nm/toluene, $\epsilon$max = 2.2 × 10$^5$), 0.1 part of a phthalocyanine compound (3-37) ($\lambda$max = 697 nm/toluene, $\epsilon$max = 2.3 × 10$^5$), 0.2 part of a phthalocyanine compound (3-38) ($\lambda$max = 695 nm/toluene, $\epsilon$max = 2.2 × 10$^5$), 0.2 part of a phthalocyanine compound (3-39) ($\lambda$max = 718 nm/toluene, $\epsilon$max = 2.1 × 10$^5$) and 0.2 part of a phthalocyanine compound (3-40) ($\lambda$max = 719 nm/toluene, $\epsilon$max = 2.1 × 10$^5$) were obtained. The structural formulae of these phthalocyanine compounds, i.e., (3-32), (3-33), (3-34), (3-35), (3-36), (3-37), (3-38), (3-39) and (3-40), are shown below:

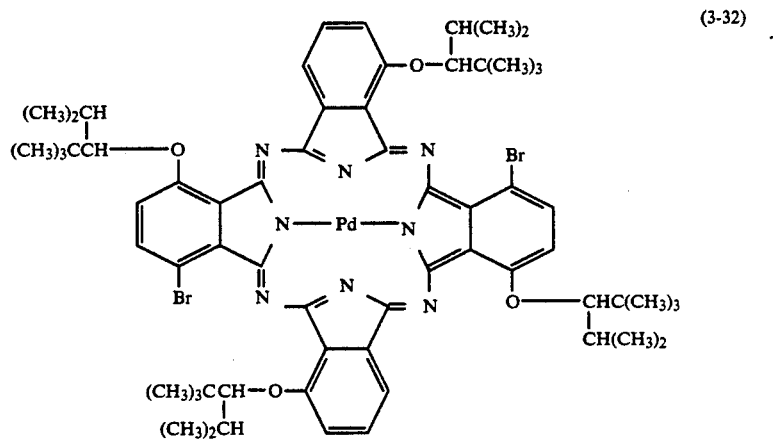
(3-32)

-continued
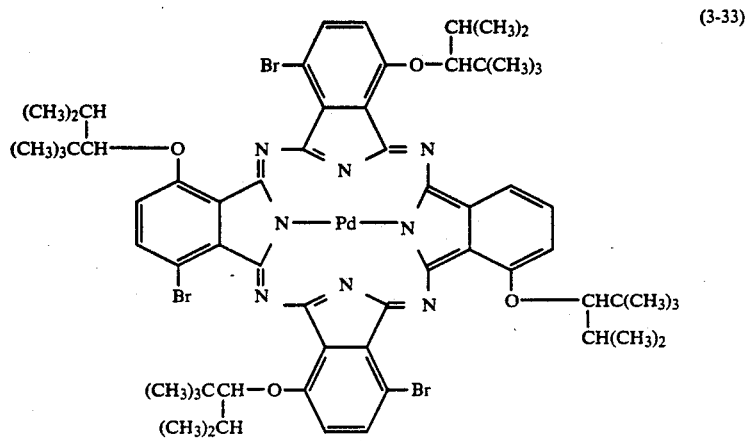
(3-33)
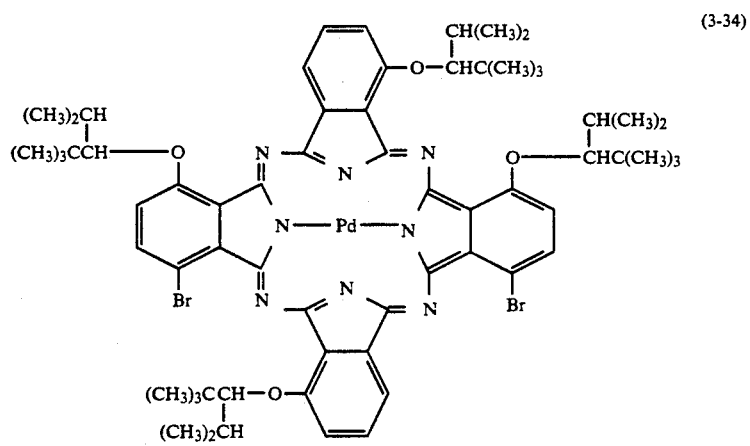
(3-34)
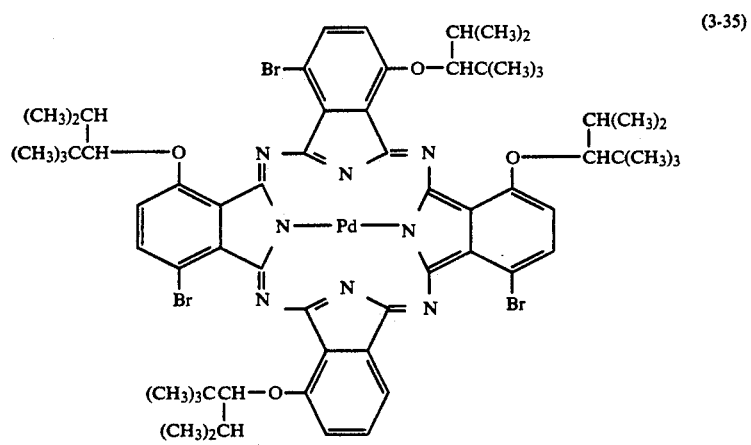
(3-35)

-continued
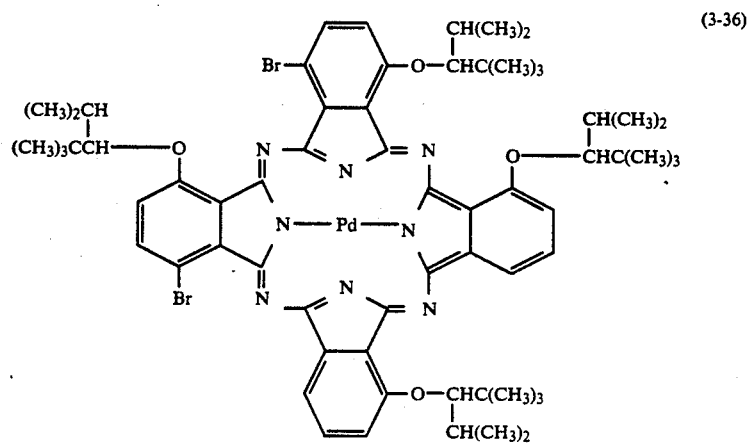
(3-36)
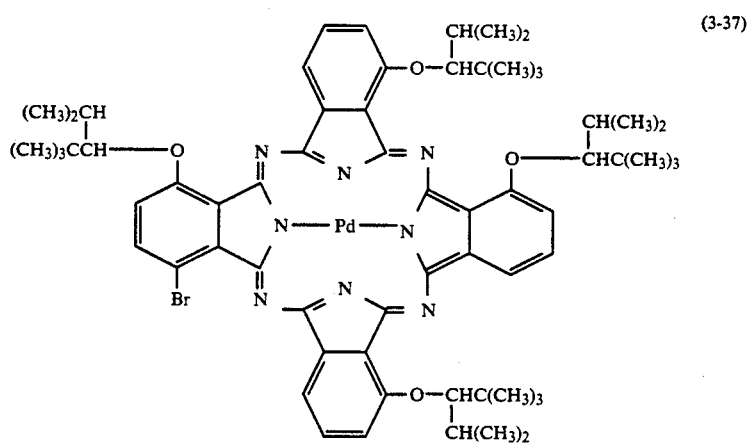
(3-37)
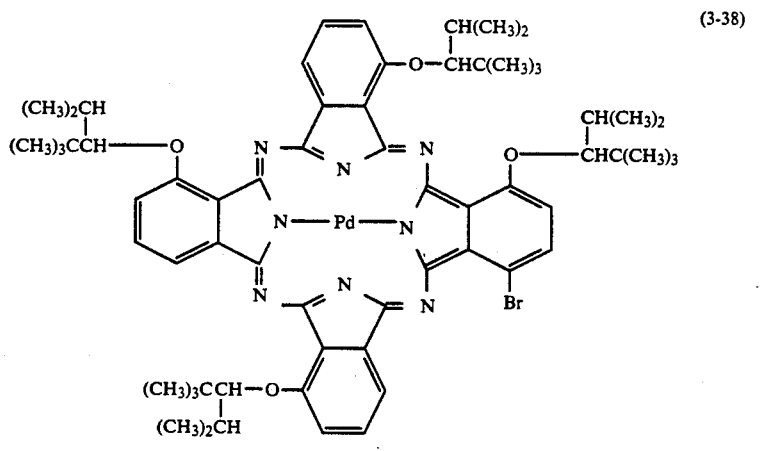
(3-38)

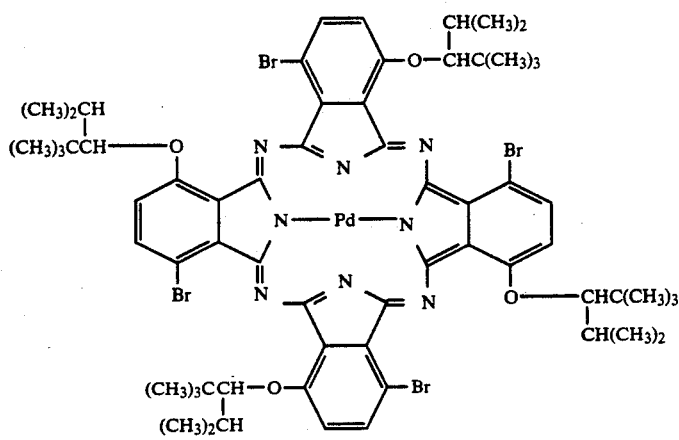

(3-39)

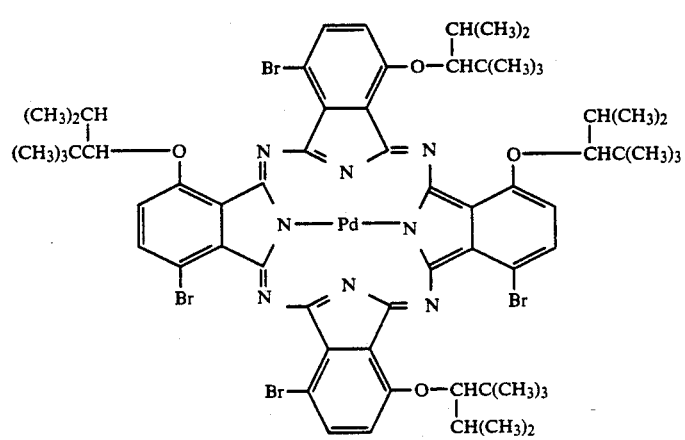

(3-40)

These phthalocyanine compopunds were identified by the element analysis and the mass spectrometry. The results are shown below.

Results of element analysis and mass spectrometry of the compound (3-32) (as Pd $C_{64}H_{78}N_8O_4Br_2$)
m/e=1289

|  | C | H | N |
|---|---|---|---|
| Found (%) | 59.11 | 5.97 | 8.51 |
| Calcd. (%) | 59.61 | 6.10 | 8.69 |

Results of element analysis and mass spectrometry of the compound (3-33) (as Pd $C_{64}H_{77}N_8O_4Br_3$)
m/e=1364

|  | C | H | N |
|---|---|---|---|
| Found (%) | 55.98 | 5.28 | 8.32 |
| Calcd. (%) | 56.16 | 5.67 | 8.19 |

Results of element analysis and mass spectrometry of the compound (3-34) (as Pd $C_{64}H_{78}N_8O_4Br_2$)
m/e=1289

|  | C | H | N |
|---|---|---|---|
| Found (%) | 59.52 | 5.96 | 8.73 |
| Calcd. (%) | 59.61 | 6.10 | 8.69 |

Results of element analysis and mass spectrometry of the compound (3-35) (as Pd $C_{64}H_{77}N_8O_4Br_3$)
m/e=1368

|  | C | H | N |
|---|---|---|---|
| Found (%) | 56.01 | 5.27 | 8.48 |
| Calcd. (%) | 56.16 | 5.67 | 8.19 |

Results of element analysis and mass spectrometry of the compound (3-36) (as Pd $C_{64}H_{78}N_8O_4Br_2$)
m/e=1289

|  | C | H | N |
|---|---|---|---|
| Found (%) | 59.33 | 5.99 | 8.45 |
| Calcd. (%) | 59.61 | 6.10 | 8.69 |

Results of element analysis and mass spectrometry of the compound (3-37) (as Pd $C_{64}H_{79}N_8O_4Br_1$)
m/e=1210

|  | C | H | N |
|---|---|---|---|
| Found (%) | 63.21 | 6.47 | 9.38 |
| Calcd. (%) | 63.49 | 6.58 | 9.26 |

Results of element analysis and mass spectrometry of the compound (3-38) (as Pd $C_{64}H_{79}N_8O_4Br_1$)
m/e=1210

|         | C     | H    | N    |
|---------|-------|------|------|
| Found (%) | 63.63 | 6.79 | 9.15 |
| Calcd. (%) | 63.49 | 6.58 | 9.26 |

Results of element analysis and mass spectrometry of the compound (3-39) (as Pd $C_{64}H_{76}N_8O_4Br_4$) m/e=1447

|         | C     | H    | N    |
|---------|-------|------|------|
| Found (%) | 53.21 | 5.47 | 7.38 |
| Calcd. (%) | 53.11 | 5.29 | 7.74 |

Results of element analysis and mass spectrometry of the compound (3-40) (as Pd $C_{64}H_{76}N_8O_4Br_4$) m/e=1447

|         | C     | H    | N    |
|---------|-------|------|------|
| Found (%) | 53.02 | 5.18 | 7.81 |
| Calcd. (%) | 53.11 | 5.29 | 7.74 |

EXAMPLE 9

A mixture of 4 parts of the diimino-iso-indoline derivative (2-1), 3 parts of a diimino-iso-indoline derivative (2-6), 3 parts of a diimino-iso-indoline derivative (2-7), 2 parts of $PdCl_2$, 4 parts of DBU and 300 parts of n-octyl alcohol was heated at 180° C. for 10 hours.

Afterward, the resulting reaction solution was poured into methanol, and the deposited tar was purified through column chromatography, so that 0.4 part of a phthalocyanine compound (3-41) (λmax=698 nm/toluene, εmax=2.3×10⁵), 0.3 part of a phthalocyanine compound (3-42) (λmax=705 nm/toluene, εmax=2.2×10⁵), 0.2 part of a phthalocyanine compound (3-43) (λmax=699 nm/toluene, εmax=2.3×10⁵), 0.2 part of a phthalocyanine compound (3-44) (λmax=707 nm/toluene, εmax=2.2×10⁵), 0.2 part of a phthalocyanine compound (3-45) (λmax=698 nm/toluene, εmax=2.2×10⁵), 0.1 part of a phthalocyanine compound (3-46) (λmax=707 nm/toluene, εmax=2.3×10⁵), 0.2 part of a phthalocyanine compound (3-47) (λmax=700 nm/toluene, εmax=2.2×10⁵), 0.2 part of a phthalocyanine compound (3-48) (λmax=707 nm/toluene, εmax=2.2×10⁵) and 0.2 part of the phthalocyanine compound (3-4) were obtained. The structural formulae of these phthalocyanine compounds, i.e., (3-41), (3-42), (3-43), (3-44), (3-45), (3-46), (3-47) and (3-48), are shown below:

-continued
(3-42)
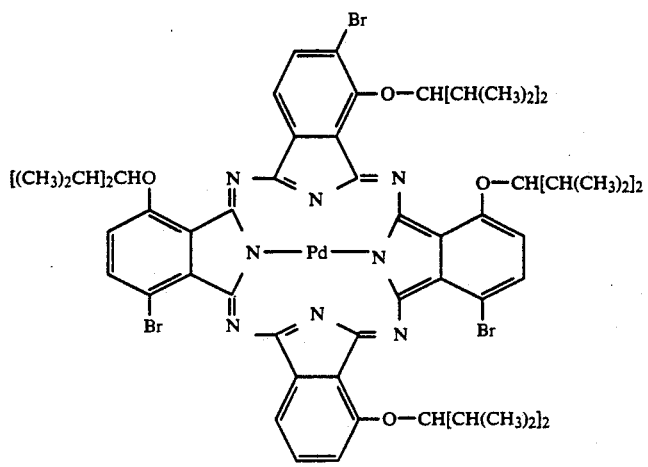
(3-43)
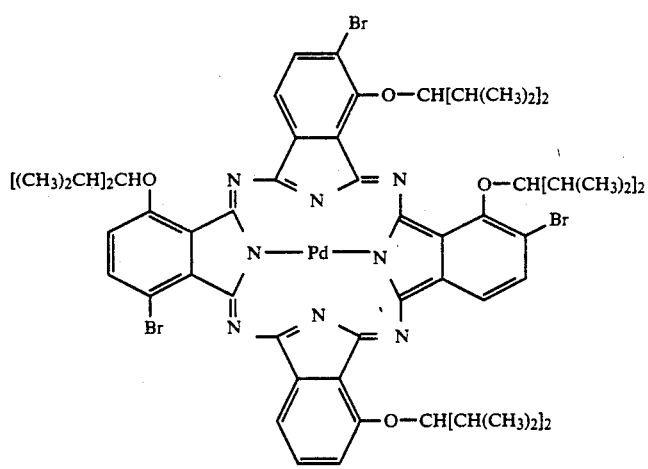
(3-44)
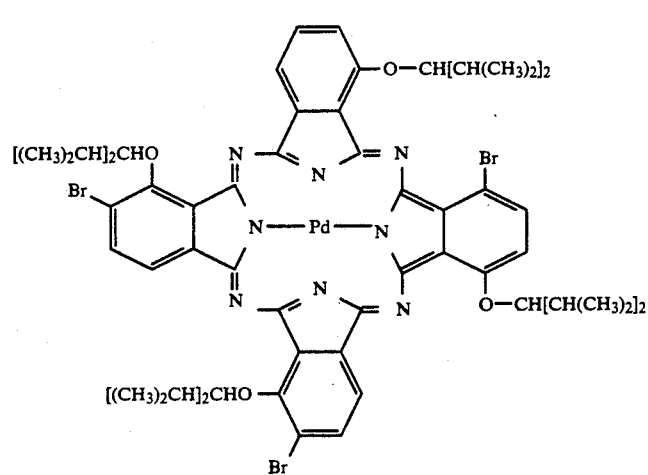

-continued
(3-45)
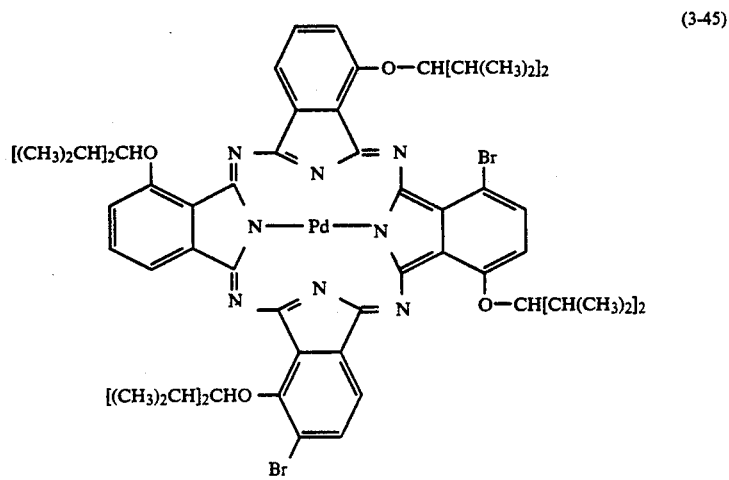
(3-46)
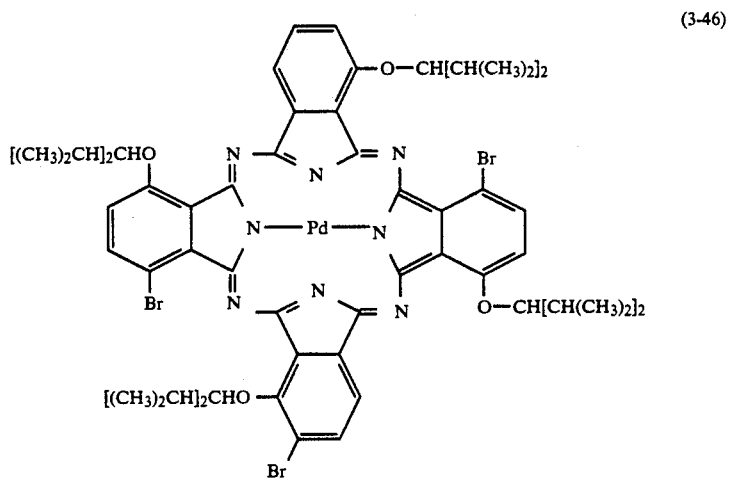
(3-47)
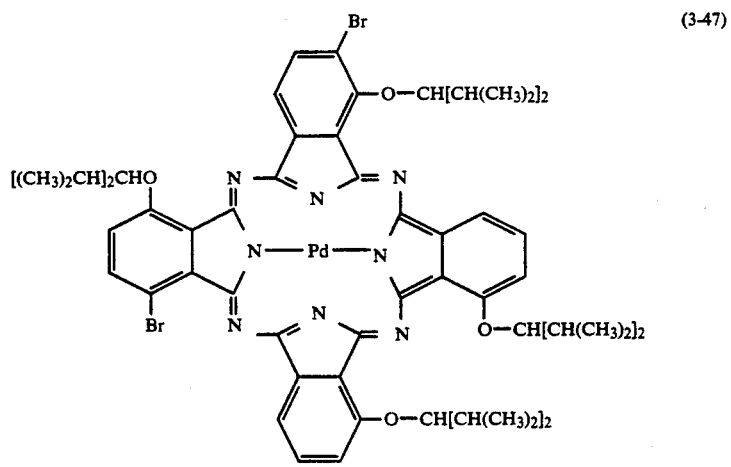

(3-48)

These phthalocyanine compounds were identified by the element analysis and the mass spectrometry. The results are shown below.

Results of element analysis and mass spectrometry of the compound (3-41) (as Pd $C_{60}H_{70}N_8O_4Br_2$)
m/e=1233

|  | C | H | N |
|---|---|---|---|
| Found (%) | 58.31 | 5.87 | 9.01 |
| Calcd. (%) | 58.42 | 5.72 | 9.08 |

Results of element analysis and mass spectrometry of the compound (3-42) (as Pd $C_{60}H_{69}N_8O_4Br_3$)
m/e=1312

|  | C | H | N |
|---|---|---|---|
| Found (%) | 54.98 | 5.28 | 8.61 |
| Calcd. (%) | 54.91 | 5.30 | 8.54 |

Results of element analysis and mass spectrometry of the compound (3-43) (as Pd $C_{60}H_{70}N_8O_4Br_2$)
m/e=1233

|  | C | H | N |
|---|---|---|---|
| Found (%) | 58.52 | 5.66 | 9.03 |
| Calcd. (%) | 58.42 | 5.72 | 9.08 |

Results of element analysis and mass spectrometry of the compound (3-44) (as Pd $C_{60}H_{69}N_8O_4Br_3$)
m/e=1312

|  | C | H | N |
|---|---|---|---|
| Found (%) | 55.01 | 5.27 | 8.48 |
| Calcd. (%) | 54.91 | 5.30 | 8.54 |

Results of element analysis and mass spectrometry of the compound (3-45) (as Pd $C_{60}H_{70}N_8O_4Br_2$)
m/e=1233

|  | C | H | N |
|---|---|---|---|
| Found (%) | 58.33 | 5.79 | 9.15 |
| Calcd. (%) | 58.42 | 5.72 | 9.08 |

Results of element analysis and mass spectrometry of the compound (3-46) (as Pd $C_{60}H_{69}N_8O_4Br_3$)
m/e=1312

|  | C | H | N |
|---|---|---|---|
| Found (%) | 55.03 | 5.51 | 8.61 |
| Calcd. (%) | 54.91 | 5.30 | 8.54 |

Results of element analysis and mass spectrometry of the compound (3-47) (as Pd $C_{60}H_{70}N_8O_4Br_2$)
m/e=1233

|  | C | H | N |
|---|---|---|---|
| Found (%) | 58.41 | 5.69 | 8.99 |
| Calcd. (%) | 58.42 | 5.72 | 9.08 |

Results of element analysis and mass spectrometry of the compound (3-48) (as Pd $C_{60}H_{69}N_8O_4Br_3$)
m/e=1312

|  | C | H | N |
|---|---|---|---|
| Found (%) | 55.01 | 5.27 | 8.48 |
| Calcd. (%) | 54.91 | 5.30 | 8.54 |

What is claimed is:
1. A halogenated alkoxyphthalocyanine represented by the formula (7)

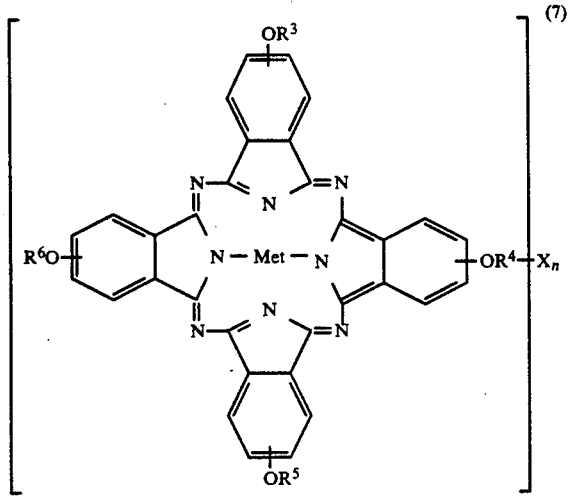

wherein R³ to R⁶ may be different and each of them is a secondary alkyl group, X is a halogen atom, n is the number of X and in the range of from 1 to 4, and Met is two hydrogen atoms, a divalent metal atom, or a member selected from the group consisting of AlY, GaY, InY, SiY₂, GeY₂, SnY₂, TiO, and VO wherein Y is Cl, Br, I or OOCCH₃, which is obtained by reacting a metal or metallic compound with one to four kinds of raw materials selected from the group consisting of phthalonitriles represented by the following formula (1)

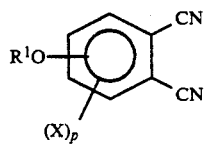
(1)

wherein R¹ is a secondary alkyl group, X is a halogen atom, and p is 0 and 1, but in at least one raw material, p is 1; and diiminoisoindolines represented by the formula (2)

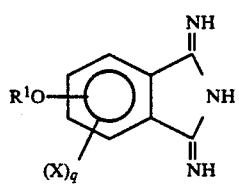
(2)

wherein R¹ is a secondary alkyl group, X is a halogen atom, and q is 0 and 1, but in at least one raw material, q is 1.

2. The phthalocyanine according to claim 1 wherein said raw material is at least one member selected from the group consisting of phthalonitriles represented by the following formulae (3) and (4) and diiminoisoindolines represented by the following formulae (5) and (6)

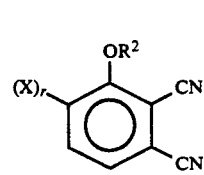
(3)

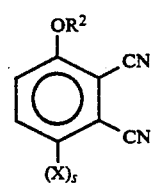
(4)

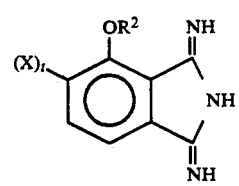
(5)

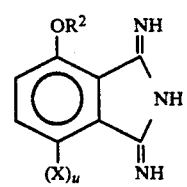
(6)

wherein R² is a secondary alkyl group, X is a halogen atom, and each of r, s, t and u is 0 or 1, but in at least one raw material, r, s, t or u is 1, and said halogenated alkoxyphthalocyanine is a mixture of at least two of compounds represented by the formulae (8) to (11)

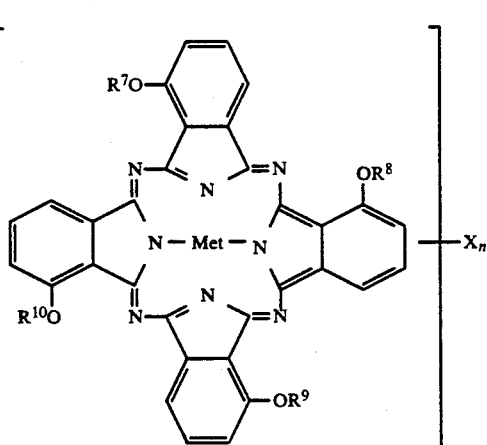
(8)

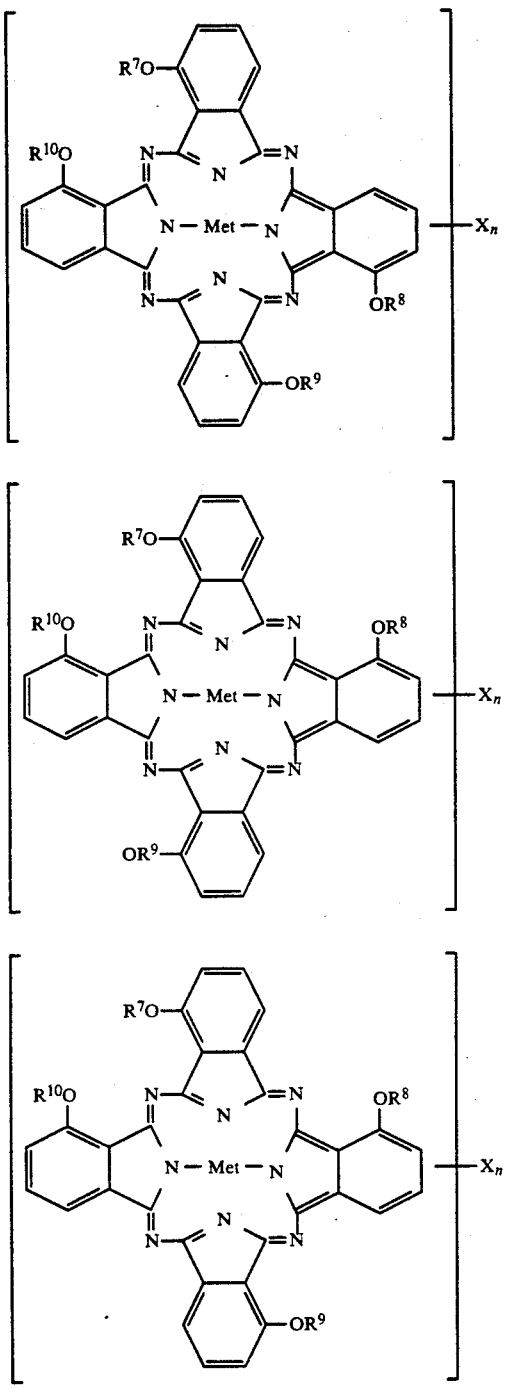

4. The phthalocyanine according to claim 3 wherein said substituent X is bromine.

5. The phthalocyanine according to claim 4 wherein said metal or said metallic compound is at least one selected from the group consisting of copper chloride, copper bromide, copper acetate, nickel chloride, nickel bromide, nickel acetate, palladium chloride, palladium bromide, palladium acetate, platinum chloride and platinum bromide.

6. The phthalocyanine according to claim 5 wherein said raw material is said phthalonitrile represented by the formula (3) or (4).

7. The phthalocyanine according to claim 5 wherein said raw material is aid diiminoisoindoline represented by the formula (5) or (6).

8. The phthalocyanine according to claim 1 wherein said raw material is at least one member selected from the group consisting of phthalonitriles represented by the following formulae (3) and (4) and diiminoisoindolines represented by the following formulae (5) and (6)

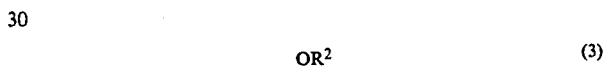

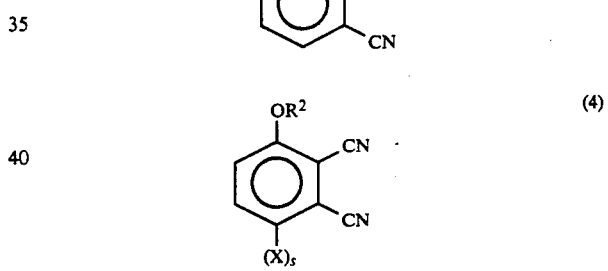

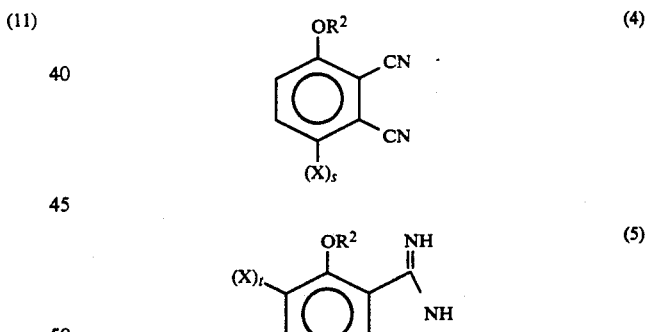

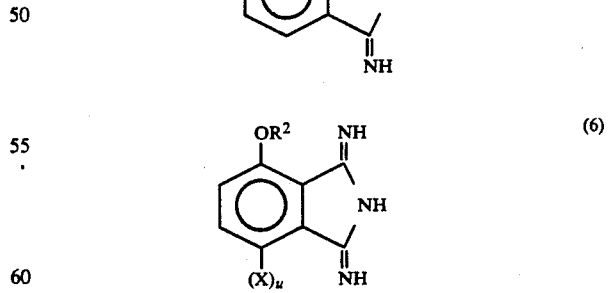

wherein each of $R^7$ to $R^{10}$ is independently a secondary alkyl group, X is a halogen atom, n is the number of X and in the range of from 1 to 4, and Met is two hydrogen atoms, a divalent metal atom, or a trivalent or a tetravalent metallic derivative or a member selected from the group consisting of AlY, GaY, InY, $SiY_2$, $GeY_2$, $SnY_2$, TiO, and VO wherein Y is Cl, Br, I or $OOCCH_3$.

3. The phthalocyanine according to claim 2 wherein said substituents of from $R^7$ to $R^{10}$ are an alkyl group having 2 to 4 secondary, tertiary or quaternary carbon atoms in total.

wherein $R^2$ is a secondary alkyl group, X is a halogen atom, and each of r, s, t and u is 0 or 1, but in at least one raw material, r, s, t or u is 1, and said halogenated alkoxyphthalocyanine is any one of phthalocyanine compounds represented by the formulae (8) to (11)

(8) 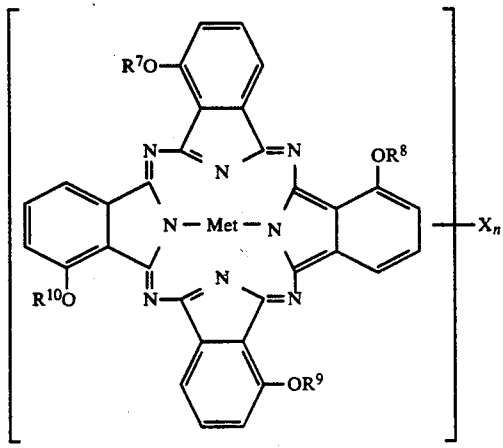

(9) 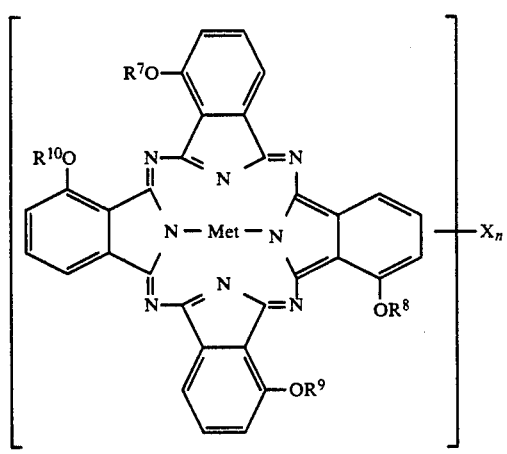

(10) 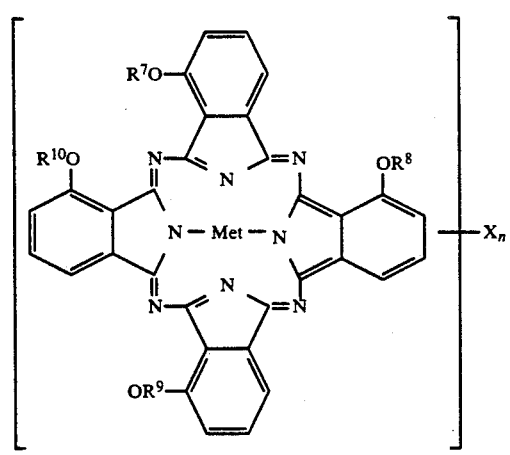

(11) 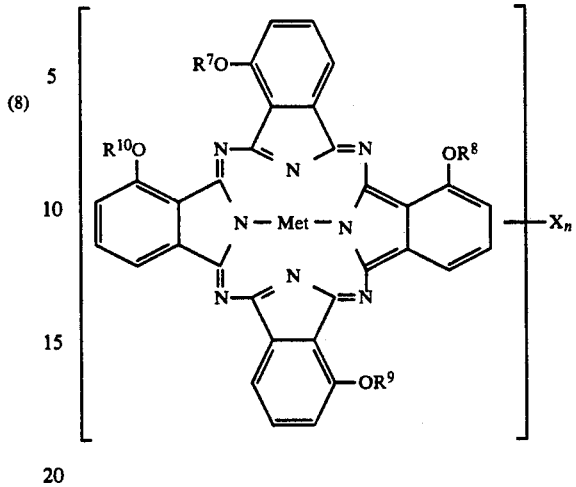

wherein each of $R^7$ is independently a secondary alkyl group, X is a halogen atom, n is the number of X and in the range of from 1 to 4, and Met is two hydrogen atoms, a divalent metal atoms, or a member selected from the group consisting of AlY, GaY, InY, $SiY_2$, $GeY_2$, $SnY_2$, TiO, and VO wherein Y is Cl, Br, I or $OOCCH_3$.

9. The phthalocyanine according to claim 8 wherein said substituents of from $R^7 R^{10}$ are an alkyl group having 2 to 4 secondary, tertiary or quaternary carbon atoms in total.

10. The phthalocyanine according to claim 9 wherein said substituent X is bromine.

11. The pathalocyanine according to claim 10 wherein said metal or said metallic compound is at least one selected from the group consisting of copper chloride, copper bromide, copper acetate, nickel chloride, nickel bromide, nickel acetate, palladium chloride, palladium bromide, palladium acetate, platinum chloride and platinum bromide.

12. The phthalocyanine according to claim 11 wherein said raw material is said phthalonitrile represented by the formula (3) or (4).

13. The phthalocyanine according to claim 11 wherein said raw material is said diiminoisoindoline represented by the formula (5) or (6).

14. A halogenated alkoxyphthalocyanine represented by any of the formulae (8) to (11)

(8) 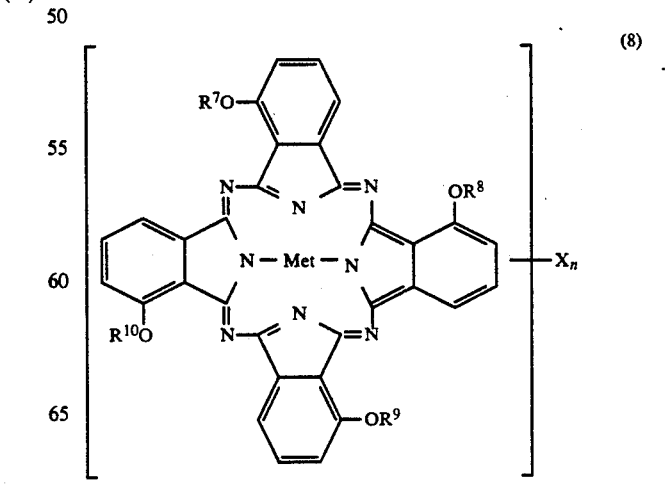

-continued

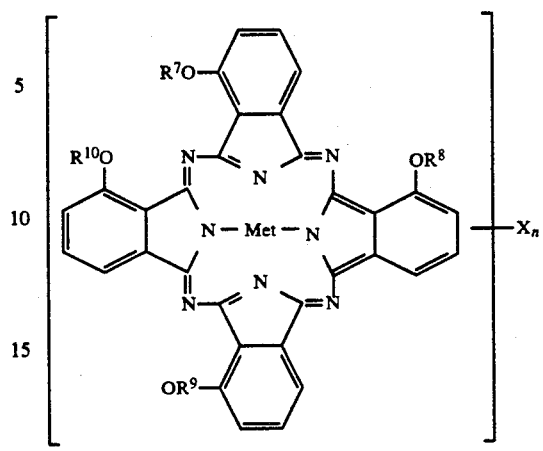
(10)

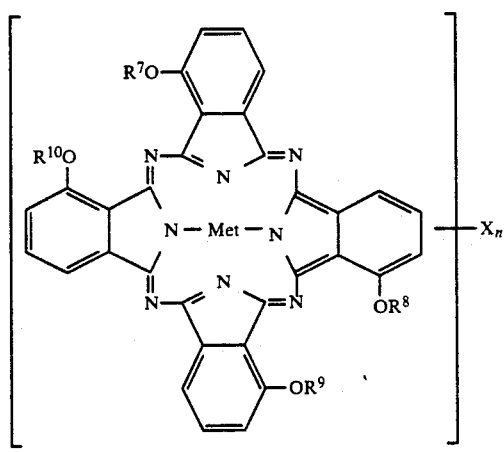
(9)

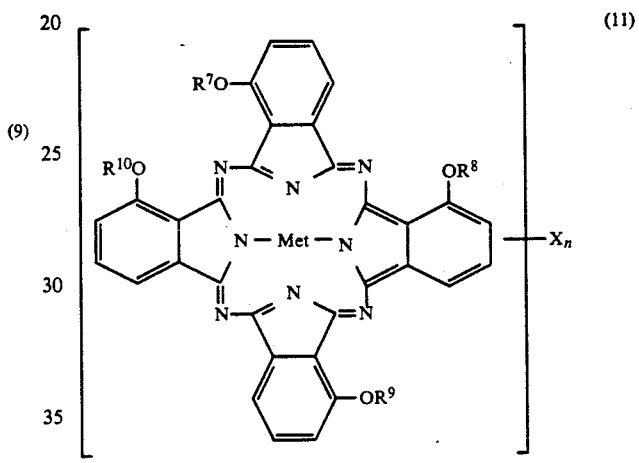
(11)

wherein each of $R^7$ to $R^{10}$ is independently a secondary alkyl group, X is a halogen atom, n is the number of X and in the range of from 1 to 4, and Met is two hydrogen atoms, a divalent metal atom, or a member selected from the group consisting of AlY, GaY, InY, $SiY_2$, $GeY_2$, $SnY_2$, TiO, and VO wherein Y is Cl, Br, I or $OOCCH_3$.

15. The phthalocyanine according to claim 14 wherein said substituents of from $R^7$ to $R^{10}$ are an alkyl group having 2 to 4 secondary, tertiary or quaternary carbon atoms in total.

16. The phthalocyanine according to claim 15 wherein said substituent X is bromine.

* * * * *